United States Patent
Foulger

(10) Patent No.: US 6,315,956 B1
(45) Date of Patent: Nov. 13, 2001

(54) ELECTROCHEMICAL SENSORS MADE FROM CONDUCTIVE POLYMER COMPOSITE MATERIALS AND METHODS OF MAKING SAME

(75) Inventor: Stephen H. Foulger, Lexington, SC (US)

(73) Assignee: Pirelli Cables and Systems LLC, Lexington, SC (US)

( * ) Notice: Subject to any disclaimer, the term of this patent is extended or adjusted under 35 U.S.C. 154(b) by 0 days.

(21) Appl. No.: 09/268,884

(22) Filed: Mar. 16, 1999

(51) Int. Cl.$^7$ .......................... G01N 27/00; G01R 27/22; H01B 1/24; C08J 9/36
(52) U.S. Cl. .......................... 422/98; 73/1.02; 73/335.05; 252/511; 264/105; 521/53
(58) Field of Search .................................. 73/31.02, 31.01; 422/98, 100, 102, 82.02; 525/106, 425; 528/411, 367; 428/323, 367; 526/279; 521/53, 54; 252/511; 264/105; 204/407, 421, 422; 205/783.5

(56) References Cited

U.S. PATENT DOCUMENTS

| 3,735,025 | 5/1973 | Ling et al. . |
| 4,265,789 | 5/1981 | Christopherson et al. . |

(List continued on next page.)

FOREIGN PATENT DOCUMENTS

| 096095 | 6/1982 | (EP) . |
| 181 587 | 5/1986 | (EP) . |
| 524 700 | 3/1988 | (EP) . |
| 337 487 | 4/1989 | (EP) . |
| 2 214 511 A | 9/1989 | (GB) . |

(List continued on next page.)

OTHER PUBLICATIONS

European Search Report No. RS 103108.
European Search Report No. RS 101469.
European Search Report No. RS 102443.
Breuer, O., et al., Segregated Structures in Carbon Black–Containing Immiscible Polymer Blends: HIPS/LLDPE Systems, pp. 1097–1106.
Graham, Gordon, et al., Insulating and Semiconductive Jackets for Medium and High Voltage Underground Power Cable Applications, *IEEE Electrical Insulation Magazine*, vol. 11, No. 5 (Sep./Oct. 1995), pp. 5–12.

(List continued on next page.)

Primary Examiner—Jill Warden
Assistant Examiner—Brian Sines
(74) Attorney, Agent, or Firm—Norris, McLaughlin & Marcus

(57) ABSTRACT

An electrochemical sensor which is tailored for sensitivity to specific chemical analytes by selecting proper constituents. The electrochemical sensor is comprised of an immiscible polymer blend of at least two polymers in which a conductive filler is dispersed in one of the polymers of the blend through a multiple percolation approach to compounding. When in the presence of a chemical analyte which is in either a liquid or vapor phase, one phase of the dual immiscible polymer blend swells, effecting a decrease in the conductivity, or increase in resistivity, of the polymer blend. The electrochemical sensor is reversible in that when the chemical analyte evaporates or is removed, the polymer blend returns to its original conductivity. With the multiple percolation approach it is possible to make a single composite material identifiably sensitive to various chemical analytes by incorporating several major phase materials into the immiscible polymer blend, each having an affinity for swelling for a different analyte. Further, the multiple percolation approach allows sensors to be made at extremely low cost.

35 Claims, 7 Drawing Sheets

U.S. PATENT DOCUMENTS

| | | |
|---|---|---|
| 4,400,580 | 8/1983 | Yamanouchi et al. . |
| 4,412,938 | 11/1983 | Kakizaki et al. . |
| 4,626,618 | 12/1986 | Takaoka et al. . |
| 4,775,500 * | 10/1988 | Funakoshi et al. . |
| 4,824,871 * | 4/1989 | Shinomura . |
| 4,929,388 | 5/1990 | Wessling . |
| 5,004,561 | 4/1991 | Nomura et al. . |
| 5,015,958 | 5/1991 | Masia et al. . |
| 5,037,999 | 8/1991 | VanDeusen . |
| 5,098,610 | 3/1992 | Okamura et al. . |
| 5,174,924 | 12/1992 | Yamada et al. . |
| 5,246,783 | 9/1993 | Spenadel et al. . |
| 5,248,553 | 9/1993 | Miyashita et al. . |
| 5,256,574 | 10/1993 | Neuburger et al. . |
| 5,281,757 | 1/1994 | Marin et al. . |
| 5,417,100 * | 5/1995 | Miller et al. . |
| 5,514,338 * | 5/1996 | Simon et al. . |
| 5,556,697 | 9/1996 | Flenniken . |
| 5,574,377 | 11/1996 | Marquez-Lucero et al. . |
| 5,672,297 | 9/1997 | Soane . |
| 5,958,303 * | 9/1999 | Narkis et al. . |
| 5,981,674 * | 11/1999 | Schomburg et al. . |
| 6,004,647 * | 12/1999 | Bambara et al. . |
| 6,048,948 * | 4/2000 | Tochioka . |
| 6,063,898 * | 5/2000 | Endo et al. . |
| 6,072,013 * | 6/2000 | Manzouji et al. . |
| 6,087,442 * | 7/2000 | LaFleur et al. . |
| 6,121,379 * | 9/2000 | Yamanaka et al. . |

FOREIGN PATENT DOCUMENTS

| | | |
|---|---|---|
| 870039181 | 8/1988 | (JP) . |
| 08 012768 | 1/1996 | (JP) . |
| WO 98/03578 | 1/1998 | (WO) . |
| WO 98/20503 | 5/1998 | (WO) . |

OTHER PUBLICATIONS

Gubbels, F., et al., Design of Electrical Conductive Composites: Key Role of the Morphology on the Electrical Properties of Carbon Black Filled Polymer Blends, *Macromolecules,* vol. 28, No. 5 (1995), pp. 1559–1566.

Kirkpatrick, Scott, Percolation and Conduction, *Reviews of Modern Physics,* vol. 45, No. 4 (Oct. 1973), pp. 574–588.

Levon, Kalle, et al., Multiple Percolation in Conducting Polymer Blends, *Macromolecules,* vol. 26, No. 15 (1993) pp. 4061–4063.

Lux, F., Review Models Proposed to Explain the Electrical Conductivity of Mixtures Made of Conductive and Insulating Materials, *Journal of Materials Science,* vol. 28 (1993), pp. 285–301.

Narkis, M., et al., Resistivity Behavior of Filled Electrically Conductive Crosslinked Polyethylene, *Journal of Applied Polymer Science,* vol. 29 (1984), pp. 1639–1652.

Narkis, M., et al., Segregated Structures in Electrically Conductive Immiscible Polymer Blends, ANTEC '95, pp. 1343–1346.

Narkis, Moshe, Structuring and Special Effects in Polymer Systems Containing Carbon Black, pp. 62–63.

Sherman, R.D., et al., Electron Transport Processes in Conductor–Filled Polymers, *Polymer Engineering and Science,* vol. 23, No. 1 (Jan., 1983) pp. 36–46.

Tchoudakov, R., et al., Conductive Polymer Blends with Low Carbon Black Loading: Polypropylene/Polyamide, *Polymer Engineering and Science,* vol. 36, No. 10 (May 1996), pp. 1336–1346.

* cited by examiner

ELECTROCHEMICAL SENSORS MADE FROM CONDUCTIVE POLYMER COMPOSITE MATERIALS AND METHODS OF MAKING SAME

BACKGROUND OF THE INVENTION

1. Field of the Invention

This invention relates to an electrochemical sensor device for detecting the presence of chemical analytes which are in either a liquid or vapor phase. More specifically, the invention relates to a reversible electrochemical sensor comprised of conductive polymer composite materials and the method of making conductive polymer composite materials for reversible electrochemical sensors.

2. Description of the Prior Art

Chemical sensing, and in particular chemical solvent sensing, has become very important for environmental and loss management concerns. The ability to detect a leak or the presence of a chemical and to identify the chemical in an inexpensive manner is of great interest. Commercial and industrial establishments concerned about gaseous emissions or chemical spills, as well as owners or operators of underground installations or utilities such as fiber optical cables, which can be damaged in the presence of chemical solvents, have a need for reliable and inexpensive chemical sensors.

Conductive polymers and conductive polymer composites have been used for chemical sensing applications because of their ability to be tailored to the chemical(s) to be sensed by a judicious choice of polymer, polymer quantities and constituents. Electrochemical sensors employing conductive polymers and conductive polymer composites often exhibit a change in conductivity in the presence of a target chemical (s). The mechanism effecting the conductivity change is often a swelling of the polymer when it absorbs the chemical or chemical vapors. This swelling alters the volume concentration of the polymer resulting in an increase in the distance between one conductive network branch to the next; therefore changing the conductivity of the polymer.

One such device is illustrated and described in U.S. Pat. No. 5,417,100 (Miller et al.) which discloses a reversible sensor for detecting solvent vapors. The sensor of the '100 patent consists of a dielectric substrate; a pair of interdigitated, electrically conductive electrodes disposed on the surface of the substrate; and a composite coating covering the interdigitated electrodes and comprising a conductive polymer and a dielectric polymer with an affinity for the solvent vapors to be detected. The sensor of the '100 patent relies on physical absorption of the vapor being detected. The absorbed vapor causes the conductive polymer composite to swell, increasing the distance between the conductive polymer chains, and therefore exhibiting a loss in conductivity, or increase of volume resistivity in the composite.

U.S. Pat. No. 5,698,089 (Lewis et al.) discloses a chemical sensor for detecting analytes in fluids. This sensor consists of a pair of conductive elements (electrical leads) coupled to and separated by a chemically sensitive resistor which provides an electrical path between the conductive elements. The resistor comprises a plurality of alternating nonconductive regions of a nonconductive organic polymer and conductive regions comprised of a conductive material. The electrical path length and resistance between the conductive regions changes with the absorption of analytes. The '089 patent also teaches of sensor arrays incorporating combinations of sensors having varied polymer and conductive polymer constituents so as to have sensitivity to a variety of analytes.

The patent to Soane (U.S. Pat. No. 5,672,297) teaches of a gel-matrix whose electrical and/or thermal conductivity undergoes a significant change in response to minor variations in one of several externally controlled thermodynamic parameters such as temperature, pH, ionic strength and solvent composition. The gel-matrix is comprised of three primary components: conductive particles, swellable and deswellable crosslinked particles, and a solvent system. In the de-swollen state, the conductive particles are normally discrete. When the gel-matrix is swollen (in response to a variation in temperature, pH, ionic strength or solvent composition), the interstitial volume between cross-linked gel particles diminishes, forcing conductive particles to come into intimate contact with one another, thus creating a more conductive network.

The heretofore discussed '100 and '089 patents prefer the use of intrinsically conductive polymers, such as polyaniline and polypyrrole, for the conductive polymer regions; while the '297 patent shows a preference for a variety of metallic and other conductive particles, including carbon black powder, for the conductive filler. The application of composite conductive polymers as electrochemical sensors using carbon black as the conductive filler has also been reported on. See for example, Lundberg and Sundqvist (1986) J.Appl.Phys. 60:1074–1079, the contents of which are incorporated by reference, which reports on the resistivity of a polyethylene matrix with a carbon black filler and a poly (tetrafluoroethylene) matrix with a carbon black filler as a function of exposure to various solvents. It was found that the resistivity of these composites increased when exposed to certain solvent vapors or were immersed in certain solvents. The report also suggests combining two or more composites with sensitivities to different analytes in a single detector, thus forming a versatile electronic sensor array.

The ability of polymers to act as electrical insulators is the basis for their widespread use in the electrical and electronic fields. However, material designers have sought to combine the fabrication versatility of polymers with many of the electrical properties of metals. A few select polymers, such as polyacetylene, polyaniline, polypyrrole and others, can be induced to exhibit intrinsic conductivity through doping, although these systems tend to be cost prohibitive and difficult to fabricate into articles. An extrinsic approach of imparting conductivity to a polymer is through the creation of conductive polymer composite ("CPC") materials. CPC materials require a random distribution of a conductive filler to be dispersed throughout an insulating polymer which results in an infinite network capable of supporting electron flow. Prior art CPC materials have employed metals, intrinsically conductive polymers, or, most often, carbon black as the conductive filler.

A crucial aspect in the production of CPC materials is the quantity of conductive filler content. If the quantity of conductive filler is too high, the processing becomes difficult, the mechanical properties of the composite are poor, and the final cost is high. Therefore, the quantity of conductive filler should be as low as possible while still allowing the composite to fulfill its electrical requirements.

Percolation theory has been successfully used to model the general conductivity characteristics of CPC materials by predicting the convergence of conducting particles to distances at which the transfer of charge carriers between them becomes probable. The percolation threshold ("$p_c$"), defined as the lowest concentration of conducting particles at which continuous conducting chains are formed, can be determined from the experimentally determined dependence of conductivity of the CPC material on the filler concentration. For a general discussion on percolation theory, see Kirkpatrick (1975) Review of Modern Physics 45:574–588, the contents of which are herein incorporated by reference. Much work has been done on determining the parameters influencing the $p_c$ with regard to the conductive filler material. See for example Lux (1993) J. Materials Sci. 28:285–301; Narkis and Vaxman (1984) J.Appl.Poly.Sci. 29:1639–1652; and Sherman and Middleman, et al. (1983) Poly.Egr. & Sci. 23:36–46; the contents of each of which are herein incorporated by reference.

A typical method of optimizing the conductive filler level to conductivity performance ratio of CPC materials is to reduce the content of the conductive filler to a value just above $p_c$. More recently, this work has been advanced by developing approaches which exploit aspects of percolation to significantly reduce $p_c$ while maintaining high levels of macroscopic conductivity. These more recent approaches realize the reduction in $p_c$ by promoting phase inhomogeneities in the total material. For example, in a binary mixture of a semicrystalline polymer and a conductive filler, the filler particles are rejected from the crystalline regions into the amorphous regions upon recrystallization, which accordingly decreases the $p_c$. Similarly, using a polymer blend with immiscible polymers which results in dual phases as the matrix in CPC materials is another alternative to promoting phase inhomogeneities and lowering the $p_c$. The heterogeneous distribution of the conductive filler within the polymers is a crucial parameter in this latter example. In one alternative of this approach, either one of the two polymer phases is continuous and conductive filler particles must be localized in the continuous phase. In a second alternative, the two phases are co-continuous and the filler is preferably in the minor phase or more preferably at the interface. These alternatives of dual continuity or "double percolation" have been reported in the scientific literature, see for example Levon and Margolina, et al. (1993) Macromolecules 26:4061–4063, the contents of which is herein incorporated by reference.

Applications of the heretofore described alternatives for reduction of conductive filler content in CPC materials have been reported for polyethylene/polystyrene immiscible blends and for polypropylene/polyamide immiscible blends, both employing carbon black as the conductive filler. See for example, Gubbels and Blacher, et al. (1995) Macromolecules 28:1559–1566; and Tchoudakov and Breuer, et al. (1996) Poly.Egr. & Sci. 36:1336–1346, the contents of both of which are herein incorporated by reference.

Accordingly, while the prior art teaches dual continuity or "double percolation" as a method for reducing the $p_c$, the prior art concerned with double percolating systems has not taught how to fully reduce the conductive filler content in CPC materials through a judicious choice of materials and various processing approaches to improve the conductive network. Further, the prior art concerned with double percolating systems has not taught or suggested how to crosslink these CPC materials. Moreover, the prior art has not recognized the potential of utilizing optimized double percolating systems for electrochemical sensors or for combining multiple sensors into one CPC by a percolation-within-percolation approach, hereinafter described.

Therefore, it is an object of the present invention to provide an electrochemical sensor whose electrical conductivity undergoes a reversible change in response to variations in solvent composition.

It is a further object of the present invention to provide a class of reversible electrochemical sensors whose sensitivity and selectivity can be tailored by a judicious choice of materials.

It is another object of the present invention to provide a reversible electrochemical sensor which incorporates multiple sensors into one CPC through a percolation-within-percolation approach to fabrication.

It is a further object of the present invention to provide a reversible electrochemical sensor, comprised of a crosslinked CPC fabricated by the percolation-within-percolation approach, whereby the sensor retains its reversibility even in environments where the sensor is subject to aggressive solvents for long periods.

It is a further object of the present invention to provide the foregoing objects with an inexpensive CPC.

It is also an object of the present invention to provide a method of making the electrochemical sensors of the foregoing objects.

The heretofore stated objects are achieved in part by basing the reversible electrochemical sensor of the present invention on a CPC material of an immiscible polymer blend having reduced conductive filler content by decreasing the p, required to generate a continuous conductive network in the CPC and by judicious selection of materials which have an affinity for swelling in the presence of a target analyte.

SUMMARY OF THE INVENTION

The invention provides an electrochemical sensor comprised of a conductive polymer composite ("CPC") of an immiscible polymer blend containing a conductive filler preferentially located in one phase. The electrical conductivity, resistivity and capacitance of the CPC will undergo a reversible change in response to exposure to chemical analytes in either a liquid or vapor phase.

The immiscible polymer blend is comprised of at least three components: (1) a conductive filler, (2) a minor phase polymer in which the conductive filler is dispersed in an amount sufficient to generate a continuous conductive network in the minor phase polymer and, (3) a major phase polymer in which the conductive filler/minor phase blend, or binary composite, is dispersed in an amount sufficient to generate a continuous conductive network in the major phase, the major phase having an affinity for a specified analyte, and the major phase being such that when mixed with the minor phase does not engage in electrostatic interactions which promote miscibility. In one embodiment of the invention, the minor/major phase blend, or ternary composite, may be dispersed in additional major phase polymers in an amount sufficient to generate a continuous conductive network in the additional major phase polymers, each additional major phase polymer having an affinity for a different analyte, and each additional major phase polymer being such that when mixed with each other, the major phase polymer and the minor phase polymer will not engage in electrostatic interactions which promote miscibility, thereby forming an electrochemical sensor of a multi-phase immiscible polymer blend which acts as multiple sensors within one CPC. Additionally, the CPC may be cross-linked via one of the major phase polymers to produce an electrochemical sensor which will retain its reversibility even in the presence of harsh solvents.

For the purposes of the present invention, the minor phase is defined as that phase of the immiscible polymer blend which has the conductive filler dispersed therein. This definition of minor phase does not preclude the minor phase from being larger by weight percent or by volume percent than the major phase polymer(s) so long as the amount of minor phase in the composite does not preclude the major phase(s) from being co-continuous. Current CPC materials require a large weight percentage of a conductive component to incur a high level of conductivity in the compound. The required high loadings of the conductive filler are a result of the probabilistic issue of generating a conductive network throughout the mixture that is infinite in cluster size. The physics of network formation of a minor second phase material in a differing major phase is effectively described by percolation theory. The level at which a minor phase is just sufficiently incorporated volumetrically into a major phase where both phases are co-continuous is termed the "percolation threshold", that is the lowest concentration of conducting particles needed to form conducting chains when incorporated into another material as heretofore described. A minor second phase material in the form of nonassociating spheres, when dispersed in a major phase material, must be in excess of approximately 16% by volume to generate an infinite network. This 16% by volume threshold is dependent on the geometry of the conductive filler particles, (i.e. the surface area to volume ratio of the particle) and will vary greatly with the type of filler. The addition of a single dispersion of conductor filler particles to a single major phase is termed "single percolation". It has been found that by altering the morphology of the minor/major phase a significant reduction in percolation threshold can be realized. The present invention exploits these aspects of percolation theory in developing very low conductive filler content CPC materials to form reversible electrochemical sensors through a number of differing methods for reducing the percolation threshold. The technique of percolating a conductive filler in a minor phase, and then consequently percolating the conductive filler/minor phase composite in a major phase is termed "percolation-within-percolation" or multiple percolation.

The systematic reduction in conductive filler required for bulk conductivity resulting from this approach is demonstrated with an example of a ternary blend. For example, two immiscible polymers can be identified; the α-polymer which is selectively filled with a conducting filler, and the β-polymer which is to be filled with the α-polymer conducting blend. Denoting the critical weight fraction or percolation threshold of the conducting filler required to insure conductivity in the α-polymer $p_{6\alpha}$ and the critical weight fraction or percolation threshold of the α-phase required to insure connectivity of the α polymer/conducting filler blend in β as $p_\beta$, the critical weight fraction of the conductive filler in the total ternary blend is $$p_c = p_{6\alpha} p_{62} \qquad (1)$$

Extending the approach to higher levels of percolation, the critical weight fraction or threshold of the conducting filler in the blend can be calculated based on the following mathematical equation:

$$p_c = p_\alpha p_\beta \cdots p_{n-1} p_n \qquad (2)$$

where $p_n$ is the threshold of co-continuity of the (n–1)-polymer blend in the n-polymer, and allows, at least theoretically, for the feasibility to obtain a conducting composite with as low a level of conductive filler as desired via multiple percolation.

In accordance with the present invention, the cost of the reversible electrochemical sensors of the present invention is low due to the optimization of conductive filler in the CPC making up the sensors by use of the multiple percolation approach to forming conductive networks. Depending on the type of conductive filler employed and the required conductivity of application, conductive filler in the amount of about 0.001% to about 25% by weight of the total composite may be employed, but in any event, a conductive filler must be incorporated in an amount sufficient to generate a continuous conductive network in the minor phase material. This reduction of conductive filler is accomplished, for example, by requiring the minor phase material to be semicrystalline and the ternary composite, (major phase/minor phase/conductive filler) to be an immiscible blend. In a binary mixture of a semicrystalline polymer and a conductive filler, the filler particles are rejected from the crystalline regions into the amorphous regions upon recrystallization, which accordingly decreases the percolation threshold. Similarly, using a polymer blend with immiscible polymers which results in dual phases as the matrix in conducting composite material promotes phase inhomogeneities and lowers the percolation threshold. The conductive filler is heterogeneously distributed within the polymers in this latter example. In one alternative of this approach, either one of the two polymer phases is continuous and conductive filler particles are localized in the continuous phase. In a second alternative, which is employed in the present invention, the two phases are co-continuous and the filler is preferably in the minor phase or more preferably at the interface.

When an insulating polymer is progressively filled with a conductive filler, the composite at the percolation threshold ("$p_c$") can exhibit an increase in conductivity of 6–12 orders of magnitude over a infinitesimally small change in the level of incorporated filler. This drastic change at $p_c$ can be exploited to design highly sensitive sensors. A composite which has a slightly larger level of conductive filler relative to $p_c$ will experience a similar decrease in conductivity when the volume of the polymer matrix is increased via solvent swelling and the "effective" volume concentration of the conductive filler is diminished. This approach can be extended in designing the sensitivity characteristics of electrochemical sensors of the present invention utilizing a multiple percolation process. For an electrochemical sensor of the present invention to have the greatest dynamic range or greatest change in conductivity in the presence of an analyte, the conductive filler content in the minor phase polymer must be equal to or slightly larger than $p_c$ for the conductive filler/minor phase pairing, while the minor phase polymer/conductive filler content dispersed in the major phase polymer must be equal to or slightly larger than $p_c$ for the minor phase/major phase pairing.

In accordance with the present invention, the conductive filler resides in a minor phase of the immiscible blend; the minor phase can be a semicrystalline polymer having a relatively high crystallinity, such as between about 20% and about 80%, and preferably for most embodiments about greater than or equal to about 70%, thereby causing the conductive filler aggregates to concentrate in amorphous regions of the minor phase or at the interface of the continuous minor and major phases.

The immiscibility of the polymer blend is at least partially guaranteed by selecting minor and major phase materials which when mixed do not engage in electrostatic interactions which promote miscibility. However, minor electrostatic interactions may be permissible with this criteria as long as miscibility is not promoted within the minor/major compositional range.

The material chosen for the conductive filler in any of the embodiments of the present invention influences the amount of conductive filler required to meet or exceed the percolation threshold ("$p_c$") to form a conductive network in the minor phase. The conductive filler may be any suitable material exhibiting conductivity and should have a chemical structure which results in an inherently high conductivity and affinity to develop a strong network.

The minor phase polymer can be a semicrystalline polymer having a relatively high crystallinity, such as between about 20% and about 80%, and preferably for most embodiments about greater than or equal to about 70% if low conductive filler content is required, but the minor phase polymer does not have to be semicrystalline.

The major phase polymer has an affinity for a specified analyte and, when mixed with the conductive filler and minor phase polymer, will not engage in electrostatic interactions that promote miscibility.

The chemical sensing aspects of the CPCs of the present invention stem from the electrical response to a dilational deformation. That is, when the CPC undergoes dilation, through swelling upon exposure to chemical analytes in either a liquid or vapor phase, the conductive cross-section of the CPC is reduced, resulting in an increase in the volume resistivity of the CPC. The dilation results in a reversible destruction of conductive paths in the CPC and is exacerbated by a mismatch in the minor and major phase solubility parameter. By altering the chemical nature of the minor/major phase and minimizing the total conductive phase, a highly selective and sensitive sensor can be fabricated for a specified analyte.

The affinity of the major phase(s) for a specified analyte for swelling is determined by the permeability of the major phase to the specified analyte. The permeability is a function of the solubility of the major phase in the specified analyte and the ability of the specified analyte to diffuse into the major phase. Thus the major phase material may be selected based on these properties as well as the desired sensitivity of the electrochemical sensor for a specific targeted analyte, keeping in mind sensitivity will also be a function of the conductive filler content's proximity to the percolation threshold.

While the swelling of the major phase is usually the primary mechanism affecting the conductivity of the CPC in the presence of a chemical analyte, other properties of the chemical analyte may contribute to the change in conductivity of the CPC. For example, certain constituents or properties of the chemical analyte may, when diffused into the major phase material, interrupt or interact with the continuous conductive network causing a reversible change in conductivity of the CPC.

The conductive polymer composites making up the electrochemical sensor of the present invention can be crosslinked to ensure the electrochemical sensor's reversibility even in the presence of aggressive solvents. The crosslinking of the conductive polymer composites of the present invention can be accomplished, for example, by choosing semicrystalline components for the minor and major phases of the composite to create a physical crosslink in the composite due to the crystalline structure of the constituent chains; or for example by irradiating the thermoplastic composite with γ-radiation or β-radiation; or for example by copolymerization or grafting a hydrolyzable group on the major phase which will effect chemical crosslinking of the final composite when introduced to moisture; or for example by chemical crosslinking with the addition of a peroxide to the major phase, thereby effecting crosslinking with the decomposition of the peroxide and subsequent generation of free radicals at elevated temperatures. More specific examples and preferred embodiments of crosslinking are described hereinafter.

In accordance with the present invention, methods to reduce conductive filler content necessary in the composite to exceed the $p_c$ and generate a continuous conductive network by a processing approach are provided. Methods to reduce conductive filler content in the CPC are accomplished by a variety of methods and combinations thereof. In one alternative, annealing the binary composite of semicrystalline polymer and conductive filler can further increase the crystalline phase and result in a lower percolation threshold for the binary composite, thereby reducing the total amount of required conductive filler in the total composite. Likewise, annealing the final composite can increase the crystalline phase and/or coarsen the morphology of the blend which reinforces the phase separation between major and minor phases and thereby improves the conductive network. In a second alternative, optimizing the surface area to volume ratio of the binary composite prior to mixing with the major phase material lowers the $p_c$ necessary to generate a continuous conductive network as heretofore described. This second alternative can be accomplished, for example, by extruding the binary composite into threads or, for example, by pulverizing the binary composite prior to mixing with the major phase, and mixing the binary composite with the major phase at a temperature lower than the melting temperature of the binary composite. More specific examples and preferred methods are described hereinafter.

The feasibility of using these composites as reversible electrochemical sensors is established using immiscible ternary blend systems of carbon black("CB"), high density polyethylene ("HDPE") and a poly(ethylene-co-vinyl acetate) ("EVA") copolymer where the CB is the conductive filler, HDPE is the minor phase polymer and EVA is the major phase polymer. The CB was dispersed into the HDPE and the CB/HDPE binary composite was dispersed into the EVA. The sensitivity of the CB/HDPE/EVA ternary composite to the presence of various analytes is demonstrated hereinafter, as is the ability to tailor the sensitivity of the CPC to a particular analyte by varying the vinyl acetate ("VA") content of the EVA.

The scope of the invention is not limited to the materials and examples hereinafter described, but to reversible electrochemical sensors based on polymeric systems that exhibit immiscibility and any conductive dispersion. The presence of an analyte in liquid or vapor form when in contact with the electrochemical sensors of the present invention can be detected by measuring the change in the electrical properties of the electrochemical sensor, such as conductivity, resistivity or capacitance.

BRIEF DESCRIPTION OF THE DRAWINGS

Other objects and advantages of the invention will become apparent upon reading the following detailed description and upon reference to the drawings in which.

DETAILED DESCRIPTION OF THE INVENTION

Figure 1:
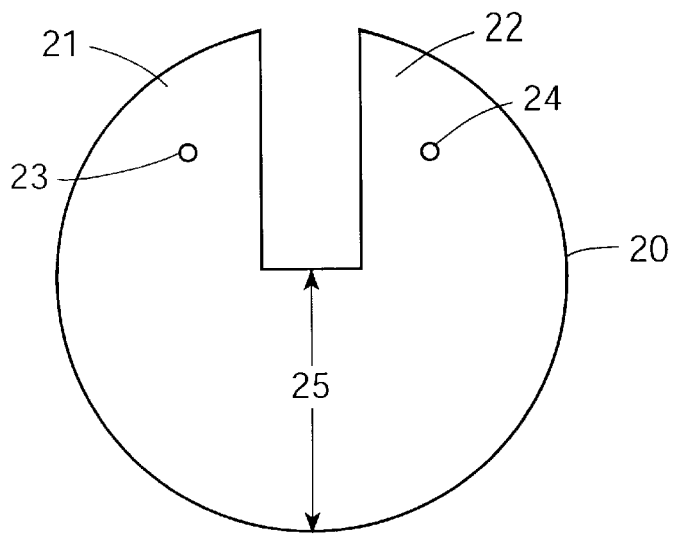
FIG. 1 is a frontal view of an embodiment of a reversible electrochemical sensor constructed according to the present invention.

Reversible electrochemical sensors of crosslinked conductive polymer composite ("CPC") materials having good conductivity with significant reduction of conductive filler content which fulfill the foregoing objects are provided in accordance with the present invention by forming an immiscible blend of a minor phase polymeric material and at least one major phase polymeric material, the minor and major phases being co-continuous, with a conductive filler residing in the minor phase or preferably at the interface of the minor and major phases; the major phases having an affinity for a specified analyte, thereby reversibly effecting the conductivity, resistivity and capacitance of the composite.

The present invention concentrates on reversible electrochemical sensors which utilize aspects of the percolation-within-percolation phenomenon which have been described in U.S. application Ser. Nos. 09/113,963 entitled "Conductive Polymer Composite Materials and Methods of Making Same"; 09/113,914 entitled "Semiconductive Jacket for Cable and Cable Jacketed Therewith"; both filed on Jul. 10, 1998 by the same applicant, and U.S. application Ser. No. 09/178,140, entitled "Crosslinked Polymer Composite Materials and Methods of Making Same," filed on Oct. 23, 1998 by the common applicant.

In accordance with the present invention, reversible electrochemical sensors are provided with a significant reduction of conductive filler content by requiring the conductive filler to be dispersed in the minor phase material, which can be a semicrystalline polymer, in an amount not more than about 5% by weight greater than the amount sufficient to generate a continuous conductive network in the minor phase material. That is, the conductive filler is dispersed in the minor phase in an amount greater than or equal to the percolation threshold ("$p_c$"), thereby forming a binary composite. The binary composite is then dispersed in at least one major phase material in an amount not more than about 5% by weight greater than the amount sufficient to generate a continuous conductive network in the major phase material, the major phase material having an affinity for at least one analyte, and the major phase material being a polymer which when mixed with the binary composite will not engage in electrostatic interactions that promote miscibility, thereby forming an immiscible CPC having co-continuous phases which will undergo a reversible change in conductivity when exposed to at least one analyte in either a liquid or vapor phase. Thus a CPC material having about 0.001% to about 25% by weight conductive filler content, and preferably less than or equal to about 10% by weight conductive filler content, and more preferably less than about 6% by weight is provided. The volume resistivity of the CPC of the electrochemical sensor of the present invention is less than about $10^8 \Omega \cdot cm$, but can be orders of magnitude less, depending on the conductive filler material chosen and the sensitivity requirements for the CPC in a specified electrochemical sensor application.

The sensitivity and dynamic range of the electrochemical sensor of the present invention is highly dependent on the both the conductive filler content with respect to the minor phase material and the amount of binary composite dispersed in the major phase polymer. When the polymer composite is designed such that the conductive filler is incorporated into the minor phase material at or just exceeding the percolation threshold, and the binary composite thus formed is dispersed in the major phase polymer at or just exceeding the percolation threshold, the swelling of the major phase polymer, or the volumetric expansion of the major phase polymer, due to the presence of a given analyte will have a greater effect on the conductivity of the composite polymer than that exhibited in a more highly conductive particle-filled composite with the same constituents in the presence of the same analyte. Therefore, when designing an electrochemical sensor of the present invention, the desired dynamic range and sensitivity should be considered when choosing how much to exceed the percolation threshold with the conductive filler content and binary composite content as a function of the total composite. The anticipated sensing environment also plays a role in this choice. Analyte vapor will not swell the composite as much as composite immersion in the same analyte. Therefore, composites designed with constituents levels very close to percolation thresholds would be desirable when analyte vapor is the expected target.

The material chosen for the conductive filler in any of the embodiments of the present invention influences the amount of conductive filler required to meet or exceed the $p_c$ required to form a conductive network when dispersed in the minor phase material. The conductive filler material may be any suitable material exhibiting conductivity and should have a chemical structure which results in an inherently high conductivity with an affinity to develop a strong network. The conductive filler may be selected from the group consisting of carbon black, graphite, metallic particles, intrinsically conductive polymers, carbon fiber, fullerenes, nanotubes, whiskers, and mixtures thereof. In particular, the carbon black may be an "acetylene black" or a "furnace black" or any commercial grade of conductive carbon black. Exemplary carbon blacks are also disclosed in the patent to Flenniken (U.S. Pat. No. 5,556,697), the contents of which are herein incorporated by reference. "Furnace blacks" are lower quality carbon blacks and are considered to be inferior in their ability to produce conductive blends when compared to "acetylene blacks", which are fabricated from the pyrolysis of acetylene. Therefore, "acetylene blacks", which are generally more expensive, are most preferred in the present invention over other carbon black types when low carbon black content is preferred over price. However, as can be seen from the hereinafter examples, "furnace blacks" are functional in producing a CPC of the present invention with less than 6% conductive filler content. Intrinsically conductive doped polymers, such as polyacetylene, polyaniline, polypyrrole, mixtures thereof, and the like, are also preferable for optimizing the reduction of conductive filler in the present invention.

The intrinsically conductive polymers are generally more costly than carbon blacks, but often have greater conductivity than many carbon blacks. Additionally, carbon filters or "whiskers" may be employed, as the amount of carbon fibers by weight percent required to exceed the percolation threshold may be equal to or even less than that of the other heretofore described suitable conductive fillers.

Suitable minor phase materials include any polymer such as, but not limited to, low density polyethylene ("LDPE"), high density polyethylene ("HDPE"), medium density polyethylene ("MDPE"), linear low density polyethylene ("LLDPE"), polypropylene ("PP"), poly-1-butene, poly(styrene)("PS"), polycarbonate ("PC"), poly(ethylene terephthalate) ("PET"), poly(hexamethylene adipamide) (nylon-6,6), poly(e-caprolactam)(nylon-6), and mixtures thereof.

One skilled in the art would recognize that the level of a minor phase material content required to meet or exceed the $p_c$ in any given major phase material is dependent on the conductive filler and the major phase material(s). The description and examples set forth herein serve as a guide. For example, it has been found that for an immiscible polymer blend having carbon black as the conductive filler, HDPE as the minor phase and poly(ethylene-co-vinyl acetate) ("EVA") as the major phase material, the vinyl acetate content of the EVA being about 9% to about 45% by weight, that the carbon black/HDPE binary blend should be greater than or equal to about 35% by weight of the total composite to result in an immiscible CPC.

Suitable major phase materials maybe any polymeric material with an affinity for a specified analyte and which does not engage in electrostatic interactions that promote miscibility in relation to the selected minor phase material. It is critical that the minor phase/major phase(s) blend is immiscible. Suitable materials for the major phase material may include, but are not limited to, for example, EVA, polybutylene terephthalate ("PBT"), PS, poly(methyl methacrylate) ("PMMA"), HDPE, LLDPE, LDPE, MDPE, PP, polyisobutylene,poly(vinyl chloride)("PVC"), poly(vinylidene chloride), poly(vinylidene fluoride) ("PVDF"), poly(tetrafluoroethylene) ("PTFE"), poly(vinyl acetate) ("PVAc"), poly(methyl acrylate), polyacrylonitrile, polybutadiene, PET, poly(8-aminocaprylic acid), nylon-6,6, poly(vinyl alcohol) ("PVA") and mixtures thereof. Note that all minor phase materials can work as major phase materials, depending on the other constituents.

One skilled in the art will recognize that the selection and amount of major phase material employed is also dependent upon other constituents of the composite and the specific application for the electrochemical sensor. The description and examples set forth herein serve as a guide. For example, exemplary minor/major pairs may include, but are not limited to, the following: minor phase materials HDPE, LLDPE, MDPE, LDPE and poly-1-butene may be paired with major phase materials EVA, PS, PVC, poly(vinylidene chloride), PTFE, PVA, PMMA, polyacrylonitrile, polybutadiene, PET, poly(8-aminocaprylic acid) and nylon-6,6. Similarly, minor phase materials PS, PC, nylon-6,6 and nylon-6 may be paired with major phase materials HDPE, LLDPE, MDPE, LDPE, PP and polyisobutylene. It is to be understood that the suitable materials and pairings of minor and major phase materials set forth herein are not exhaustive, and that those skilled in the art of polymer science and engineering will recognize that an infinite number of materials and pairings are possible based on the criteria heretofore described for selection of suitable minor and major phase materials.

When the electrochemical sensor of the present invention is expected to be exposed to aggressive solvents, the CPC making up the electrochemical sensor of the present invention may be crosslinked via one of the major phase polymers so that it will retain its reversibility. There are a number of methods for effecting crosslinking of ternary composites as hereinafter described.

In one embodiment of the invention, crosslinking is accomplished in the CPC by selecting the major phase material and the minor phase material to have a crystallinity of between about 20% to about 80%. A physical crosslink is then effected when the minor phase semicrystalline polymer, having a crystallinity of about 20% to about 80%, of the binary composite is mixed with the major phase material. For example, a minor phase material of HDPE having a crystallinity of up to about 80% and a major phase material of nylon-6,6 having a crystallinity of up to about 72%, when mixed according to the present invention, will effect a physical crosslinking. As an additional example, a minor phase material of HDPE and a major phase material of EVA with a low VA content (less than about 28% by weight) will promote crystallinity in the ethylene sections of the copolymer while still retaining a sufficient quantity of the VA to maintain immiscibility with the HDPE, effecting a physical crosslink of the CPC. One skilled in the art will know of other examples of materials which will physically crosslink.

In a second embodiment of the invention, crosslinking can be achieved by exposing the CPC to β or γ radiation for a sufficient time, as is known in the art, to effect crosslinking.

In a third embodiment of the invention, crosslinking can be achieved by grafting a hydrolyzable group onto the major phase material by adding a silane group, a catalyst, and an organic peroxide to the major phase material prior to dispersing the binary composite therein such that the CPC will crosslink on exposure to moisture. In an alternative to this embodiment, the major phase material may be a commercially available copolymer which contains a hydrolyzable functionality as part of the copolymer backbone. For example, polyethylene-co-vinyl silanes are suitable commercially available major phase materials available from Union Carbide Corporation as DFDA 5451 and from AT Plastics as Aqua-Links® 910 and 920. In another alternative to this embodiment, a hydrolyzable copolymer may be created during the mixing process of producing the CPC by grafting an unsaturated moiety containing one or more hydrolyzable functionalities to the major phase polymer backbone prior to dispersing the binary composite in the major phase. In general, members of the homologous series of $Si(OR)_3$ such as vinyltriethoxysilane, vinyltris(2-methoxyethoxy)silane, or preferably vinyltrimethoxy silane ("VTMO") can be used. The grafting reaction may, for example, be peroxide initiated using peroxides such as t-butyl peroxide, or preferably dicumyl peroxide ("DCP"), or others as known in the art. The crosslinking is accomplished in moisture in the in the presence of a catalyst such as dioctyltin maleate, dibutyltin diacetate, stannous acetate, lead naphthalate, zinc caprylate, or preferably dibutyltin dilaurate ("DBTL") which can be added to the major phase material during the grafting.

In a fourth embodiment, crosslinking can be achieved by adding an organic peroxide such as DCP;2,5-dimethyl-2,5-di(t-butylperoxy)hexane;t-butyl cumyl peroxide; 2,5-dimethyl-2,5-di(t-butylperoxy)hexane-3; or others to the major phase material prior to the dispersion of the binary composite therein; thereby effecting crosslinking with the decomposition of the peroxide and subsequent generation of free radicals at elevated temperatures. In this fourth embodiment it may be preferable that the organic peroxide be added to the major phase material before the binary composite is added in order that the organic peroxide has sufficient time to be absorbed by the major phase material before mixing the binary composite with the major phase material. Alternatively, the organic peroxide can be absorbed onto a pelletized CPC.

In accordance with the present invention, in order to form two sensors within one CPC, which will further reduce the conductive filler content needed in the CPC, and/or to tailor the CPC to a specific application, the CPC may further comprise a second major phase material wherein the ternary composite (consisting of the binary composite dispersed in the first major phase material), is dispersed in an amount sufficient for the ternary composite to be continuous within the second major phase material. The second major phase material being a polymer which has an affinity for a second specified analyte and the second major phase material being selected from that group of polymers which when mixed with the ternary composite will not engage in electrostatic interactions that promote miscibility with the minor phase material or with the major phase material, thus forming a conductive immiscible quaternary composite having co-continuous phases which undergoes a reversible loss of conductivity when exposed to either of at least two analytes. The quaternary composite may be crosslinked via either the first or second major phase material as heretofore discussed.

The quaternary composite has preferably less than about 4% by weight conductive filler content with respect to the total quaternary composite weight, yet forms a continuous conductive network due to the multiple percolation of the quaternary composite. For example, a quaternary composite of the present invention could be formed with a conductive filler of a "furnace black" type carbon black dispersed in a minor phase of HDPE; the carbon black comprising about 3.6% by weight of the quaternary composite and the HDPE comprising about 26.4% by weight of the quaternary composite. The major phase material being EVA, having an affinity for swelling in the presence of THF, in the amount of about 30% by weight of the quaternary composite and the second major phase material being PS, having an affinity for swelling in the presence of toluene, in the amount of about 40% by weight of the quaternary composite Or, for example, to produce a physically crosslinked quaternary composite, using carbon black as the conductive filler, EVA with a low VA content (less than about 25%) as the minor phase material, nylon-6,6 having an affinity for swelling in the presence of sulfuric acid as the major phase material, and the second major phase material being HDPE having an affinity for swelling in the presence of hexane. Other combinations meeting the requirements of the present invention will be apparent to those skilled in the art.

In a like manner, electrochemical sensors of the present invention can be formed with more than two major phase materials in order to make multiple sensors in one CPC. The requirements for selection of each additional major phase material are the same as for the quaternary composite heretofore described. That is, the additional major phase materials are selected for their affinity for additional chemical analytes, and additional major phase materials must be selected such that when mixed with the CPC already formed they will not engage in electrostatic interactions that promote miscibility with the minor phase material, the major phase material, or the second major phase material, such that an immiscible polymer blend with co-continuous phases is formed. Further, the amount of the CPC dispersed in the additional major phase materials must be sufficient to be continuous with the additional major phase materials.

One skilled in the art will recognize that the amount of ternary composite sufficient for the ternary composite to be continuous in additional major phase materials, or the amount of quaternary composite sufficient for the quaternary composite to be continuous in additional major phase materials, is dependent upon the constituents of the composite system, and may be determined experimentally by measuring volume resistivity as a function of ternary or quaternary composite content to ensure that the final composite is conductive. For quaternary composites and composites having more than two major phase materials, all primary constituents (i.e., conductive filler, minor phase material, and major phase materials) must be mutually insoluble for the temperature and conditions of the composite use.

Crosslinking of quaternary and additional major phase composites may be accomplished by the means heretofore described for ternary composites; however, the grafting of hydrolyzable groups or the addition of organic peroxides for crosslinking should be done in-one or more of the major phases and preferably in the most major phase of the composite.

In accordance with the present invention, other additives may be included in any of the heretofore described embodiments in order to enhance physical or other properties depending on the ultimate application for the CPC. For example, typical additives which can be introduced include: antioxidants, coupling agents, ultraviolet absorbers or stabilizers, pigments, dyes, nucleating agents, reinforcing fillers or polymer additives, slip agents, plasticizers, processing aids, lubricants, viscosity control agents, tackifiers, anti-blocking agents, surfactants, extender oils, metal deactivators, voltage stabilizers, flame retardant fillers and additives, crosslinking agents, boosters and catalysts, and smoke suppressants. Fillers and additives can be added in amounts ranging from less than about 0.05% to more than about 50% by weight of the total composite. The amount of the additives in the composite will correspondingly decrease the weight percent of other constituents required in the composite to maintain the properties described in the present invention.

Exemplary nucleating agents are talc, silica, mica and kaolin. Exemplary antioxidants are: hindered phenols such as tetrakis[methylene(3,5-di-t-butyl4-hydroxyhydrocinnamate)]-methane, 4,4'-thiobis(2-methyl-6-t-butylphenol), and thiodiethylene bis(3,5-di-t-butyl-4-hydroxy)hydrocinnamate;phosphites and phosphonites such as tris(2,4-di-t-butylphenyl)phosphite; thio compounds such as dilaurylthiodipropionate, dimyristylthiodipropionate and distearylthiodipropionate; various siloxanes; and various amines such as polymerized 2,2,4-trimethyl-1,2-dihydroquinoline and the like. Antioxidants can be used in an amount of about 0.05 to about 2 weight percent of the total composite.

In accordance with further embodiments of the present invention, methods of producing a reversible electrochemical sensor of the present invention are provided, including several embodiments to reduce the amount of conductive filler required to generate a continuous conductive network in the binary composite and thus in the final CPC through processing approaches to multiple percolation.

In a first method of producing the electrochemical sensor of the present invention, a minor phase polymer having a melting temperature is mixed in a mixer, wherein the mixer is preheated to at least the melting temperature of the minor phase polymer. A conductive filler is added to the minor phase polymer in the mixer in an amount greater than or equal to an amount required to generate a continuous conductive network in the polymer. The conductive filler and the minor phase polymer are mixed for a time and at a sufficient speed to insure uniform distribution of the conductive filler in the minor phase polymer, thereby forming a conductive binary composite having a melting temperature. A major phase polymeric material having a melting temperature and selected such that when mixed with the binary composite will not engage in electrostatic interactions which promote miscibility, is then mixed with the binary composite in the mixer for a time and at a sufficient speed to insure a uniform distribution of the binary composite in the major phase material such that a weight ratio of the binary composite to the major phase material is sufficient for the binary composite to be equal to or greater than an amount required to generate a continuous conductive network in the major phase material, wherein the mixer is preheated to at least the melting temperature of the binary composite and the major phase material, such that a conductive immiscible ternary composite with co-continuous phases is formed. The ternary composite may be crosslinked by means heretofore described.

One method of crosslinking the ternary composite according to the present invention, is accomplished by selecting the major phase material and the minor phase polymer to have a crystallinity of between about 20% and about 80%, such that a physical crosslink is effected when the semicrystalline polymer of the binary composite is mixed with the major phase material.

In a second method of crosslinking the ternary composite in accordance with the present invention, the crosslinking step comprises irradiating the ternary composite with β- or γ-radiation, for a sufficient time to effect crosslinking of the composite.

In a third method of crosslinking the ternary composite in accordance with the present invention, the crosslinking step comprises grafting a hydrolyzable group onto said major phase material by adding a silane group, a catalyst, and an organic peroxide to the major phase material prior to mixing the major phase material and the binary composite, and thereafter exposing the ternary composite to moisture to crosslink the ternary composite.

In a fourth method of crosslinking the ternary composite in accordance with the present invention, the crosslinking step is accomplished by selecting the major phase material from commercially available copolymers which include a hydrolyzable functionality as part of the copolymer backbone, and exposing the ternary composite to moisture to effect a chemical crosslink.

In a fifth method of crosslinking the ternary composite in accordance with the present invention, the crosslinking step comprises adding an organic peroxide to the major phase material prior to mixing the major phase material with the binary composite, whereby the ternary composite crosslinks over time. In this fifth method, it may be preferable, that the organic peroxide be added to the major phase material in a mixer before the binary composite is added to the mixer in order that the organic peroxide has sufficient time to be absorbed by the major phase material before mixing the binary composite with the major phase material. Alternatively, the peroxide can be absorbed onto the pelletized ternary compound. Crosslinking is effected with the decomposition of the peroxide and subsequent generation of free radicals at elevated temperatures. The decomposition of the peroxide occurs more quickly at higher temperatures.

In one alternative it has been found, as in Example 2 set forth hereinafter, that if the crosslinking occurs too quickly, then the composite may have to go through a post-crosslinking heating process after compounding to induce phase separation and/or recrystallization, thereby making the composite conductive. In thermoplastic conductive immiscible composites of the present invention and described in heretofore referenced U.S. application Ser. No. 09/113,963, annealing the conductive immiscible ternary composite clearly resulted in morphological changes in the ternary composite, enhancing the conductivity. In the present alternative, no clear morphological changes have been seen due to the post-crosslinking heating, although morphological changes may occur on a local level or below the level of optical resolution depending on the crosslink density employed. However, we have found experimentally that the crystallinity of the minor phase increased by about 5% after a post-crosslink heating at 150° C. for 15 hours, which is most likely indicative of a reorganization in the minor phase, resulting in an increase of the conductive cross-section of the composite. In a second alternative, it has been found that the post-crosslinking heating process is not necessary if the composite is heated to less than or equal to about 175 C to induce phase separation before the crosslinking is completed.

In accordance with the present invention, the method of producing an electrochemical sensor may further comprise mixing a second major phase material having a melting temperature, with the ternary composite, in a mixer preheated to about the melting temperatures of the second major phase material and of the ternary composite for a time and at a sufficient speed to insure a uniform distribution of the ternary composite in the second major phase material, such that a weight ratio of the ternary composite to the second major phase material is sufficient for the ternary composite to be equal to or greater than an amount required to generate a continuous conductive network in the second major phase material. The second major phase material is selected from that group of polymers which when mixed with the ternary composite will not engage in electrostatic interactions which promote miscibility with the binary composite or with the major phase material, such that a conductive immiscible quaternary composite with co-continuous phases is formed. The quaternary composite may be crosslinked by methods heretofore described. However, in this embodiment it is preferable than when crosslinking of the composite by means of inclusion of a hydrolyzable group or by the addition of an organic peroxide, inclusion of the hydrolyzable group and addition of the organic peroxide be done to the second major phase material.

The CPCs making the electrochemical sensor of the present invention can be further enhanced to reduce the conductive filler content by conventional annealing processes. Preferably, the annealing processes hereinafter described should be accomplished before crosslinking the CPC or before the crosslinking is complete. That is, in accordance with a further embodiment of the present invention, the heretofore described binary composite, ternary composite and/or quaternary composite may be annealed, thereby coarsening the morphology of the respective composite and resulting in a more conductive composite and/or increasing the crystallinity of the composite. For example, the $p_c$ of the binary composite in the major phase may be reduced by preferably annealing the final CPC from approximately just above the melting temperature of both the binary composite and the major phase material(s).

Alternatively, according to the present invention, the $p_c$ of the conductive filler in the polymer may be reduced by selecting a semicrystalline polymer for the minor phase polymer and by annealing the binary composite before mixing with the major phase material. The annealing will result in the threshold concentration for forming conductive networks in the binary composite to be lower. During the crystallization process, a major part of the conductive filler particles are rejected into interspherulitic boundaries and the remaining, non-rejected conductive filler particles may be located in amorphous regions within the spherulites, resulting in the heretofore described reduction in the $p_c$. Thus annealing of the binary composite refines and increases the crystalline phase. The binary composite may be annealed to below the binary composite's melting temperature prior to mixing the major phase material with the binary composite, wherein the major phase material has a melting temperature less than the binary composite's melting temperature. The major phase material and the binary composite being mixed at a temperature below the melting temperature of the binary composite.

In a further embodiment of the present invention, a reduction of the $p_c$ of the binary composite in the major phase material may be achieved by modifying the surface area to volume ratio of the binary composite, thereby increasing the binary composite's affinity to create a conductive network, before mixing the binary composite with the major phase material. This can be accomplished by pulverizing the binary composite or more preferably by extruding threadlike structures of binary composite prior to mixing the binary composite with the major phase material. The threadlike structures of binary composite may, for example, be about 2 mm long and about 0.25 mm in diameter. The extrusion of the binary composite into threadlike structures being done by conventional extrusion techniques as is known in the art. The pulverized or threadlike structures of binary composite are then mixed with the major phase material below the melting temperature of the binary composite.

The principles of the present invention are further illustrated by the following non-limiting examples.

EXAMPLE 1

A reversible electrochemical sensor based on a thermoplastic CPC material having reduced carbon black content was made according to the present invention using commercial grades of a random copolymer of poly(ethylene-co-vinyl acetate) ("EVA"), HDPE, and furnace grade carbon black. The characteristics of the materials used in this example are set forth in Table 1.

The CPC material was mixed in the weight percentages set forth in Table 1 at 170° C. in a Brabender internal mixer with a 300 cm³ cavity using a 40 rpm mixing rate. The mixing procedure for the ternary composites comprises adding the HDPE into the preheated rotating mixer and allowing the polymer to mix for 6 minutes prior to the addition of the carbon black. After the addition of the carbon black, the compound is mixed for an additional 9 minutes, which insures a uniform distribution of carbon black within the HDPE. The EVA is added and the mixture allowed to mix for an additional 10 minutes.

TABLE 1

| Constituent | Amount (w/w) | Tradename | Characteristics | Producer |
|---|---|---|---|---|
| EVA | 50 | Elvax 263 | 28 weight % VA content | DuPont |
| HDPE | 44 | Petrothene LS6081-00 | density = 0.963 g/cm³ | Millennium Chemical |
| carbon black | 6 | Vulcan XC72 | $N_2$ Surface Area = 254 m²/g DBP oil absorption = 174 cm³/100 g mean particle diameter = 300 Angstroms | Cabot Corp. |

The final compound was then molded at a pressure of about 6 MPa for 12 minutes at 170° C. into plaques of about 0.75 mm in thickness.

An electrochemical sensor in the shape of a disc 20, shown in FIG. 1, having a diameter of 2.9 cm and thickness of 0.18 cm was cut from the molded plaques. A rectangular section measuring 0.65 cm×1.45 cm was cut from one side of the electrochemical sensor extending to the approximate center of the disc forming flanges 21 and 22. Colloidal silver paint was used to fabricate electrodes 23 and 24 on the flanges 21 and 22 of the electrochemical sensor 20 in order to remove the contact resistance. A Fluke 75 Series II digital multimeter and a 2 point technique was used to measure the electrical resistance of the electrochemical sensor 20 at room temperature.

The measured volume resistivity for the electrochemical sensor was 279 Ω·cm. The percolation threshold of this EVA/HDPE/CB composite is about 4.2% by weight carbon black and is significantly lower than that of the individually carbon filled HDPE or EVA. Thus, the 6% by weight carbon black loading of the composite of the present example is above the percolation threshold of the EVA/HDPE/CB composite.

Figure 2:
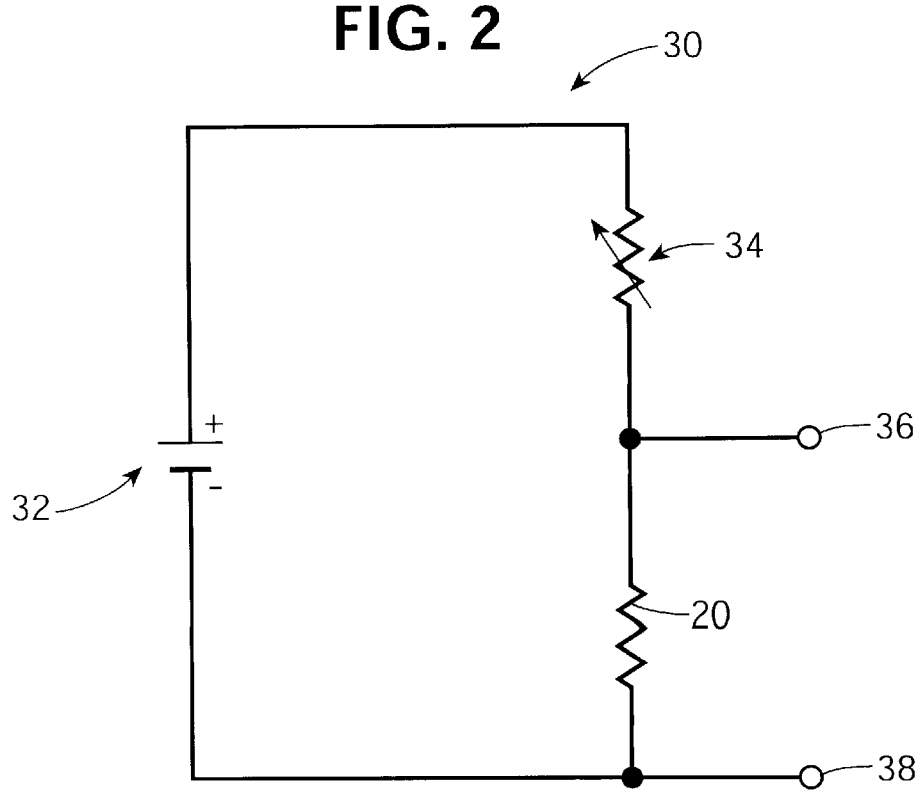
FIG. 2 is the electrical circuit used to assess the response of reversible electrochemical sensors constructed according to the present invention upon exposure to an analyte.

The electrochemical sensor 20 was placed in the test circuit 30 depicted in FIG. 2. The test circuit 30 is a simple voltage divider where the voltage source 32 (5 V D C) was split unevenly between the tunable standard resistance 34 and the electrochemical sensor 20. Initially, the tunable standard resistance was adjusted to have 4.9 V appear across it, while the remaining 0.1 V appeared across the electrochemical sensor 20 as measured across leads 36 and 38. Once the electrochemical sensor was immersed in a solvent, to the depth 25 indicated in FIG. 1, and began to increase in volume resistivity, the 5 V split between the tunable standard resistance 34 and the electrochemical sensor 20 automatically adjusted to reflect the increased resistance of the electrochemical sensor. The response of the electrochemical sensor in the presence of various analytes over time was measured by lowering the electrochemical sensor 20 into an analyte to a depth of half the diameter 25 of the electrochemical sensor disc 20 with the electrodes 23 and 24 protruding out of the analyte and not in contact with the analyte and measuring the resistance of the electrochemical sensor 20 over the immersion time in the analyte. The leads, 36 and 38, were attached to an analog/digital board for data acquisition and storage by a personal computer.

Figure 3:
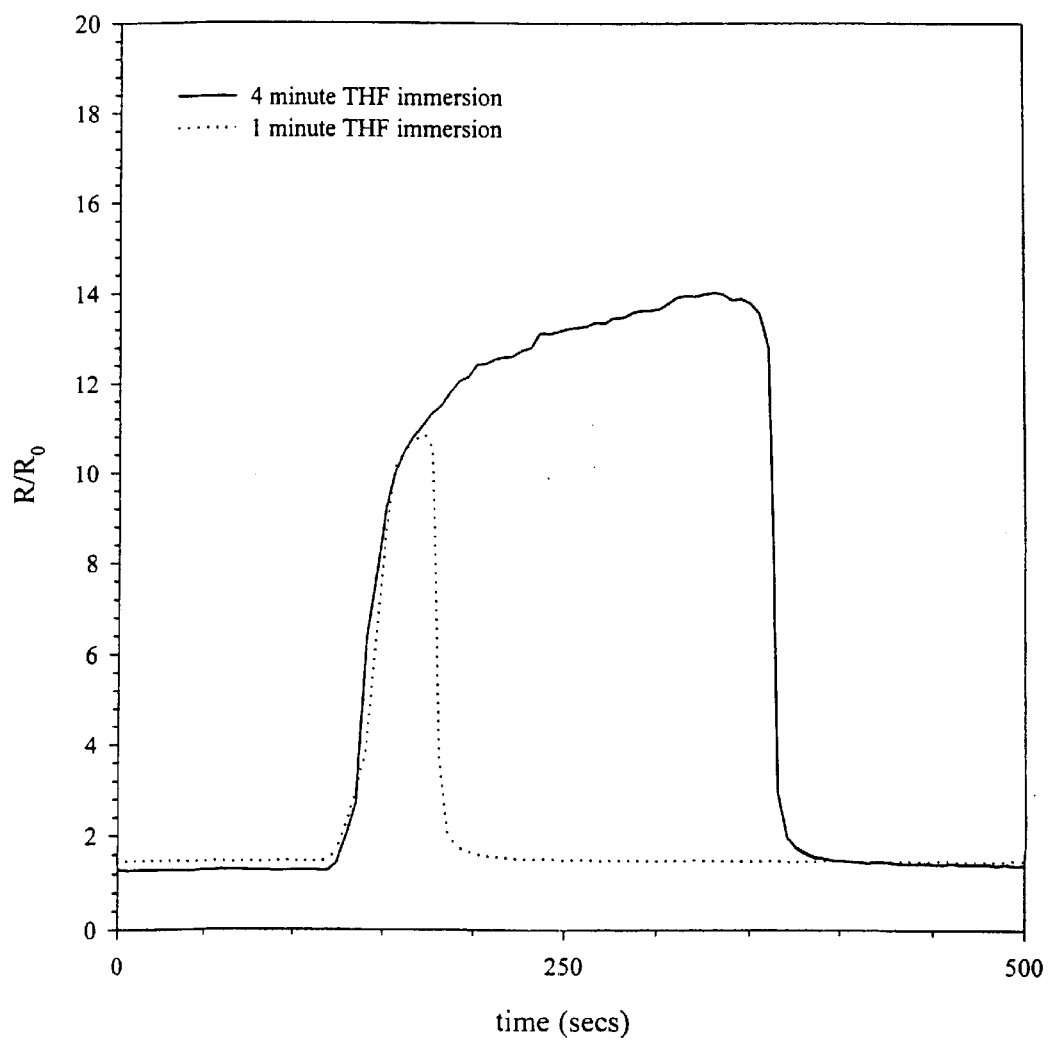
FIG. 3 is a graph depicting the electrochemical response over time of a CB/HDPE/EVA conductive polymer composite, constructed according to the present invention, upon immersion in tetrahydrofuran ("THF").
Figure 4:
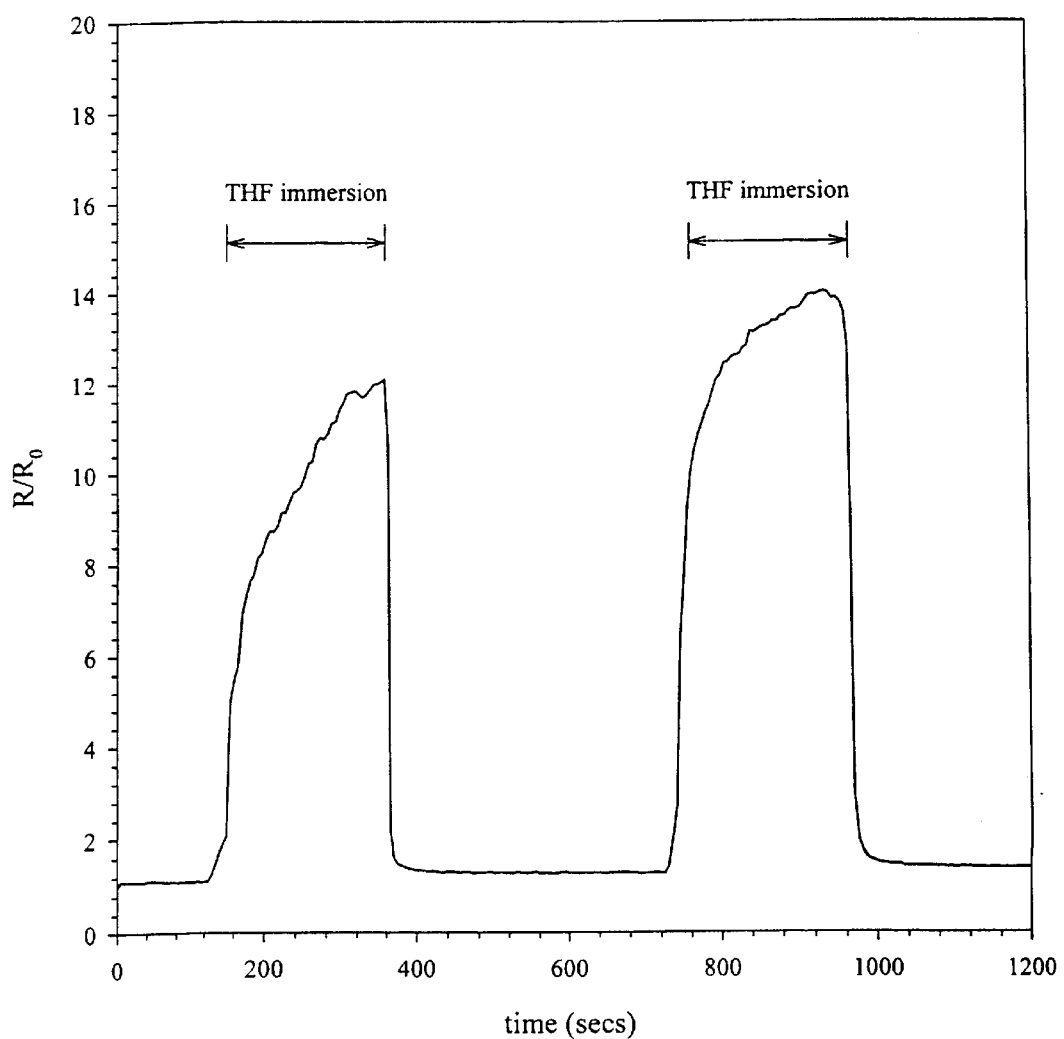
FIG. 4 is a graph depicting the reproducibility of the electrochemical response of the sensor of FIG. 1 upon multiple immersions in THF.

The electrochemical sensor of the present example was placed as heretofore described in a bath of tetrahydrofuran ("THF"). FIG. 3 shows the increase in resistivity of the electrochemical sensor of the present example for immersion times of 1 minute and 4 minutes in the THF. As can be seen from FIG. 3, the resistivity of the electrochemical sensor increases almost an order of magnitude during the immersion time, but reverts to the original resistivity shortly after being removed from the THF. FIG. 4 shows the electrochemical response of the electrochemical sensor of the present example for repeated immersions in THF, demonstrating the reproducibility of the sensor response.

Figure 5:
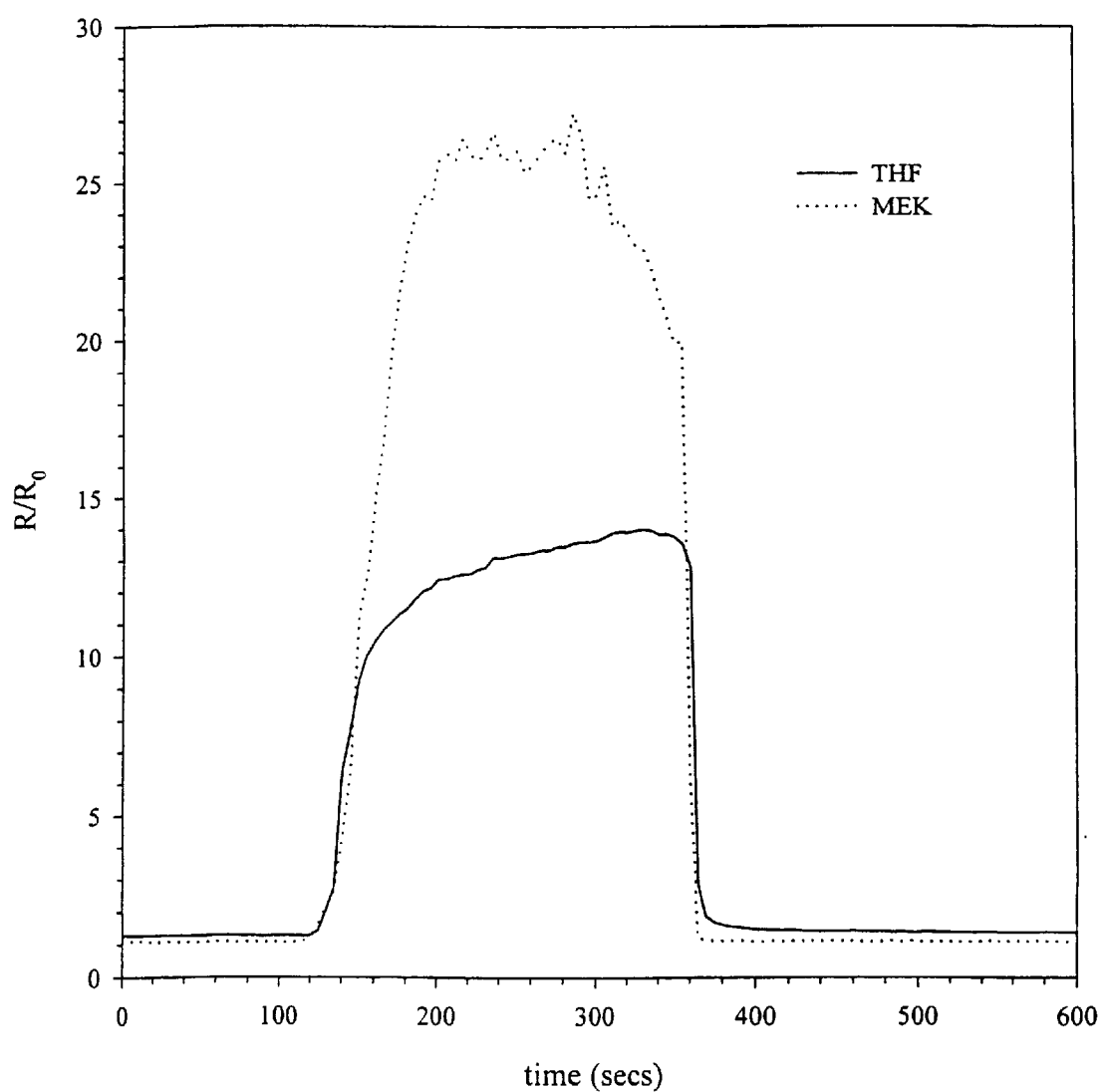
FIG. 5 is a graph depicting the electrochemical response over time of a CB/HDPE/EVA conductive polymer composite, constructed according to the present invention, upon immersion in methyl ethyl ketone ("MEK"), said response being superimposed on the response of the same electrochemical sensor when immersed in THF.

FIG. 5 shows the response of the electrochemical sensor of the present example when immersed in methyl ethyl ketone ("MEK") superimposed on the response of the same electrochemical sensor immersed in THF. It can be seen from FIG. 5 that the analyte can be identified by the electrochemical response of the composite.

The foregoing example particularly demonstrates the reversibility and selectivity to different analytes of the electrochemical sensor of the present invention.

EXAMPLE 2

Reversible electrochemical sensors based on a thermoplastic CPC material having reduced carbon black content were made according to the present invention using commercial grades of a random copolymer of poly(ethylene-co-vinyl acetate) ("EVA"), HDPE, and furnace grade carbon black using the mixing procedure and electrochemical sensor disc preparation as heretofore described in Example 1. In the present example, the vinyl acetate content of the EVA and the weight percent ratios of EVA to HDPE/CB in the composite were varied, while maintaining a 12% by weight ratio of CB to HDPE, in order to demonstrate the sensitivity of the electrochemical sensor can be tailored to an analyte. The characteristics of the materials used and weight %'s for each composite for the present example are set forth in Table 2.

TABLE 2

| composite designation | ethylene-co-vinyl acetate copolymer (DuPont Elvax) (w/w) | vinyl acetate content (w/w) | high density polyethylene (w/w) (Quantum LS6081-00) | carbon black (w/w) (Cabot XC-72) |
|---|---|---|---|---|
| JQ01-P25-5 | 50.0 | 28 | 44.0 | 6.0 |
| JQ01-P23-2 | 50.0 | 25 | 44.0 | 6.0 |
| JQ01-P24-4 | 50.0 | 18 | 44.0 | 6.0 |
| JQ01-P31-6 | 50.0 | 15 | 44.0 | 6.0 |
| JQ01-P32-9 | 40.0 | 25 | 52.8 | 7.2 |
| JQ01-P32-8 | 40.0 | 18 | 52.8 | 7.2 |

Table 3 sets forth the electrochemical response of the composites of the present example and indicates a positive increase in resistivity with immersions times in tetrahydrofuran ("THF") for all composites. For ternary composites with the same composition but incorporating various levels of vinyl acetate ("VA") in the EVA, (JQ01-P25-5 to JQ01-P31-6), the decrease in VA tends to diminish the response of the sensors. Now comparing composites JQ01-P23-2 to JQ01-P32-9 and composites JQ01-P24-4 to JQ01-P32-8, Table 3 shows that moderately increasing the percentage of HDPE/CB in the composition results in a composite with a similar room temperature volume resistivity, but a drastic increase in sensitivity to the THF.

TABLE 3

| composite | $\rho_0 (\Omega \cdot cm)$ at 23° C. | $R/R_0$ after 1 minute of immersion in THF | $R/R_0$ after 5 minute of immersion in THF |
|---|---|---|---|
| JQ01-P25-5 | $2.79 \times 10^2$ | 8.591 | 11.199 |
| JQ01-P23-2 | $8.36 \times 10^2$ | 6.972 | 14.873 |
| JQ01-P24-4 | $4.32 \times 10^3$ | 5.642 | 13.985 |
| JQ01-P31-6 | $5.88 \times 10^3$ | 7.475 | 11.451 |
| JQ01-P32-9 | $5.86 \times 10^2$ | 546.004 | 801.648 |
| JQ01-P32-8 | $1.72 \times 10^3$ | 308.934 | 416.415 |

Figure 6:
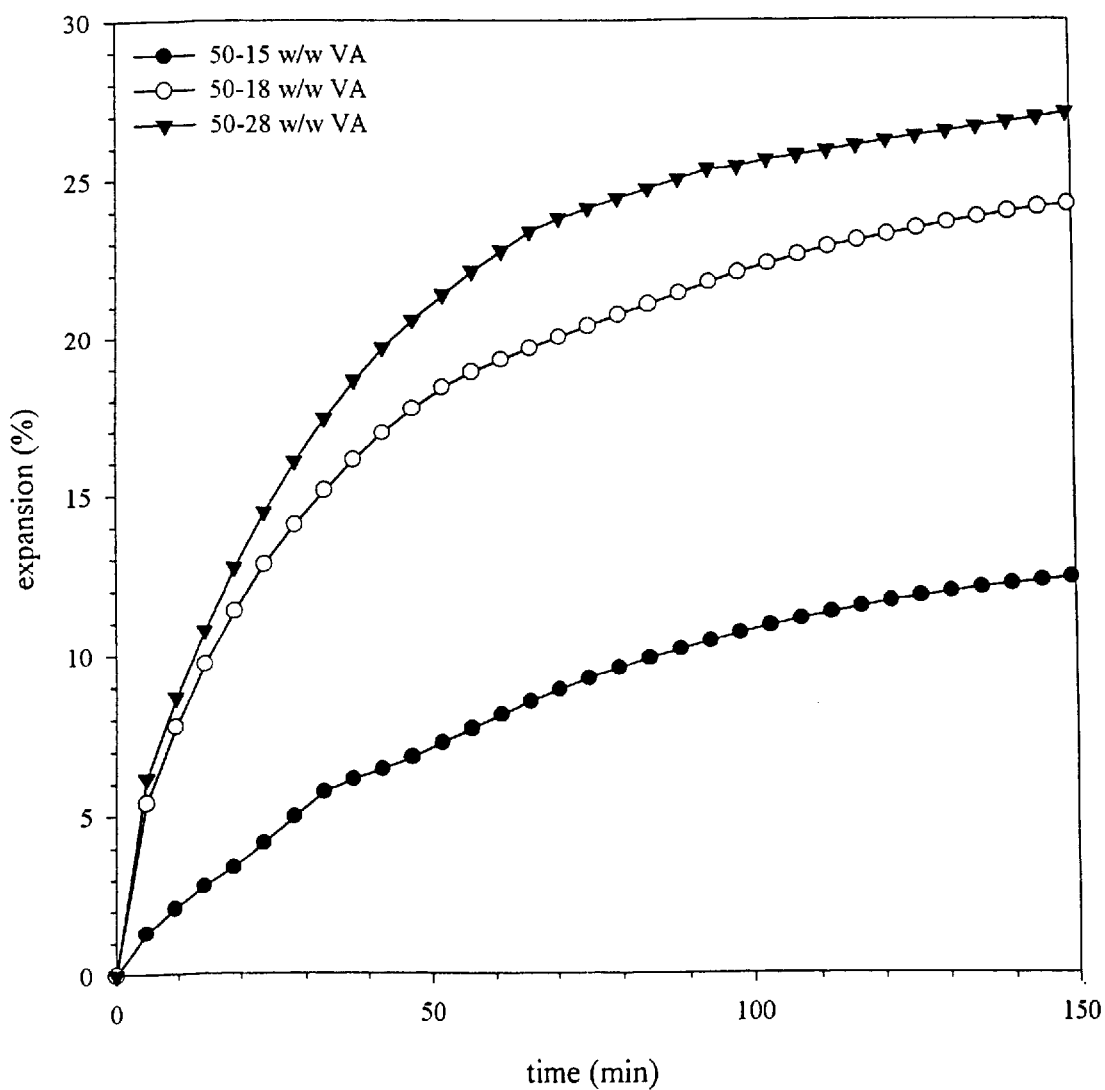
FIG. 6 is a graph depicting the volumetric expansion over time of CB/HDPE/EVA conductive polymer composites with varying VA contents, constructed according to the present invention, upon immersion in THF.

As heretofore described, the composite swells when immersed in an analyte, reducing the conductive cross section of the composite, and resulting in an increase in the volume resistivity of the composite. The swelling results in a reversible destruction of conductive paths in the composites and is exacerbated by a mismatch in the minor and major phase solubility parameter. A volumetric expansion of the composite corresponds to the reversible destruction of the conductive paths in the composite. FIG. 6 graphically depicts the volumetric expansion of composites JQ01-P25-5, JQ01-P24-4, and JQ01-P31-6 as a function of time of immersion in THF. It can be seen from FIG. 6, that increasing the VA content in the EVA corresponds to a greater volumetric expansion of the composite for a given immersion time, demonstrating the proposed role of expansion in increasing sensitivity of the composite to an analyte with increasing VA content. This volumetric response correlates with the resistivity data for composites JQ01-P25-5 to JQ01-P31-6 set forth in Table 3. It must be noted that volumetric expansion is not the only measure or mechanism for increased sensitivity. A different analyte or different weight % of constituents could yield a different dominant mechanism for increased sensitivity.

The present example demonstrates how the sensitivity of the composite can be tailored for a given solvent by varying composition and weight % of constituents.

EXAMPLE 3

A reversible electrochemical sensor based on a crosslinked CPC material having reduced carbon black content was made according to the present invention using commercial grades of a random copolymer of poly(ethylene-co-vinyl acetate) ("EVA"), HDPE, and furnace grade carbon black. The crosslinking means of the present example was accomplished by mixing an organic peroxide to the major phase material, EVA, and crosslinking the EVA at elevated temperatures to form a conductive polymer composite. The characteristics of the materials used in this example are set forth in Table 4.

TABLE 4

| composite | ethylene-co-vinyl acetate copolymer (DuPont Elvax) (w/w) | vinyl acetate content (w/w) | high density polyethylene (w/w) (Quantum LS6081-00) | carbon black (w/w) (Cabot XC-72) | 2,5-dimethyl-2,5-di-t-butylperoxy-hexyne-3 (w/w) (Elf Atochem Luperox 130) |
|---|---|---|---|---|---|
| JQ01-P38-TS1 | 49.8 | 28 | 44.0 | 6.0 | 0.2 |

All composites were mixed in a Brabender Banbury mixer with a 300 cm$^3$ cavity using a 72 RPM (200 s$^{-1}$ shear rate).

The mixing procedure for producing the binary conducting polymer composite comprises: preheating the mixer to 170° C.; measuring out 200 grams of HDPE and 27.2 grams of the carbon black; adding half of the HDPE to the preheated rotating mixer; adding the remaining half of the HDPE in two steps to the rotating mixer as the HDPE softened; mixing the HDPE in the mixer for 6 minutes; adding the measured out carbon black to the mixing HDPE; and mixing the HDPE/CB blend for 9 minutes. The mixer was then turned off and the binary composite (HDPE/CB blend) was removed from the mixer while still hot. After the binary composite cooled to room temperature, the binary composite was chopped into pieces having approximately 0.75" maximum major axis, in order to ease the mixing of the ternary composite.

The mixing procedure for producing the ternary composite comprises: measuring out 100 grams of the EVA, 100 grams of the HDPE/CB blend, and 0.4 grams of peroxide; preheating the mixer to 140° C.; adding the EVA to the preheated rotating mixer; mixing the EVA in the mixer for 30 seconds; adding the peroxide to the EVA in the mixer as the stock temperature of the EVA began to rises; preheating the HDPE/CB blend to approximately softening point in order to facilitate mixing; mixing the peroxide with the EVA for approximately 1.5 minutes, which allows the peroxide to be absorbed into the EVA; adding the preheated HDPE/CB blend to the EVA in the mixer once the stock temperature of the EVA reached 130° C.; and mixing the HDPE/CB/EVA blend for an additional 5 minutes. The mixer was then shut down and the ternary composite was removed from the mixer while still hot. The ternary composite was cooled, then chopped into approximately 0.75" pieces and molded into 0.075" thick plaques at 190° C. using between about 40 grams to about 50 grams of material for each plaque.

The plaques were then heated to about 150° C. for about 15 hours in a vacuum oven in order to induce phase separation of the HDPE phase and the EVA phase. In this example it is important to note that the binary composite formed was conductive; however, the crosslinked ternary composite had a volume resistivity of approximately $10^{12}$ Ω·cm and was not conductive until the heating process was complete. The Lupersol 130 peroxide has a half-life of ca. 1.5 minutes at 1 90° C. and will crosslink the EVA completely in about 4.5 to about 7.5 minutes at this temperature. Therefore, molding the composite plaques at this elevated temperature crosslinks the composite before the morphology of the composite has a chance to coarsen. The post-crosslink heating allows the local level morphology of the composite to coarsen and increase the crystallinity of the minor phase, thus enhancing the conductivity of the composite.

It should be noted in the present example that certain preparation steps, for example, chopping the binary composite and preheating the binary composite prior to mixing with the EVA, are done merely to facilitate the mixing process. The times and speeds of mixing were used to ensure uniform distribution of the blend, and other parameters could be used as is known in the art.

The electrochemical sensor disc with a pair of electrodes as is known in the art was prepared as heretofore described in Example 1. The disc was measured for resistivity and subsequently immersed in THF to determine the electrochemical response of the sensor. Table 5 sets forth the electrical properties of the crosslinked conductive ternary composite formed in this example of the present invention before and during immersion in THF.

TABLE 5

| composite | $\rho_0$(Ω · cm) at 23° C. | $R/R_0$ after 1 minute of immersion in THF | $R/R_0$ after 5 minute of immersion in THF |
|---|---|---|---|
| JQ01-P38-TS1 | $6.02 \times 10^3$ | 1.525 | 12.239 |

The JQ01-P38-TS1 composite of the present example is a crosslinked version of JQ01-P25-5 of Example 2. In comparing sensitivity of the crosslinked and thermoplastic composites, the Tables (3 & 5) show that the crosslinked composite, JQ01-P38-TS1, has a lower sensitivity and has applications where more aggressive solvents are more likely to be present, or where immersion in even a mild analyte would likely be prolonged.

Figure 7:
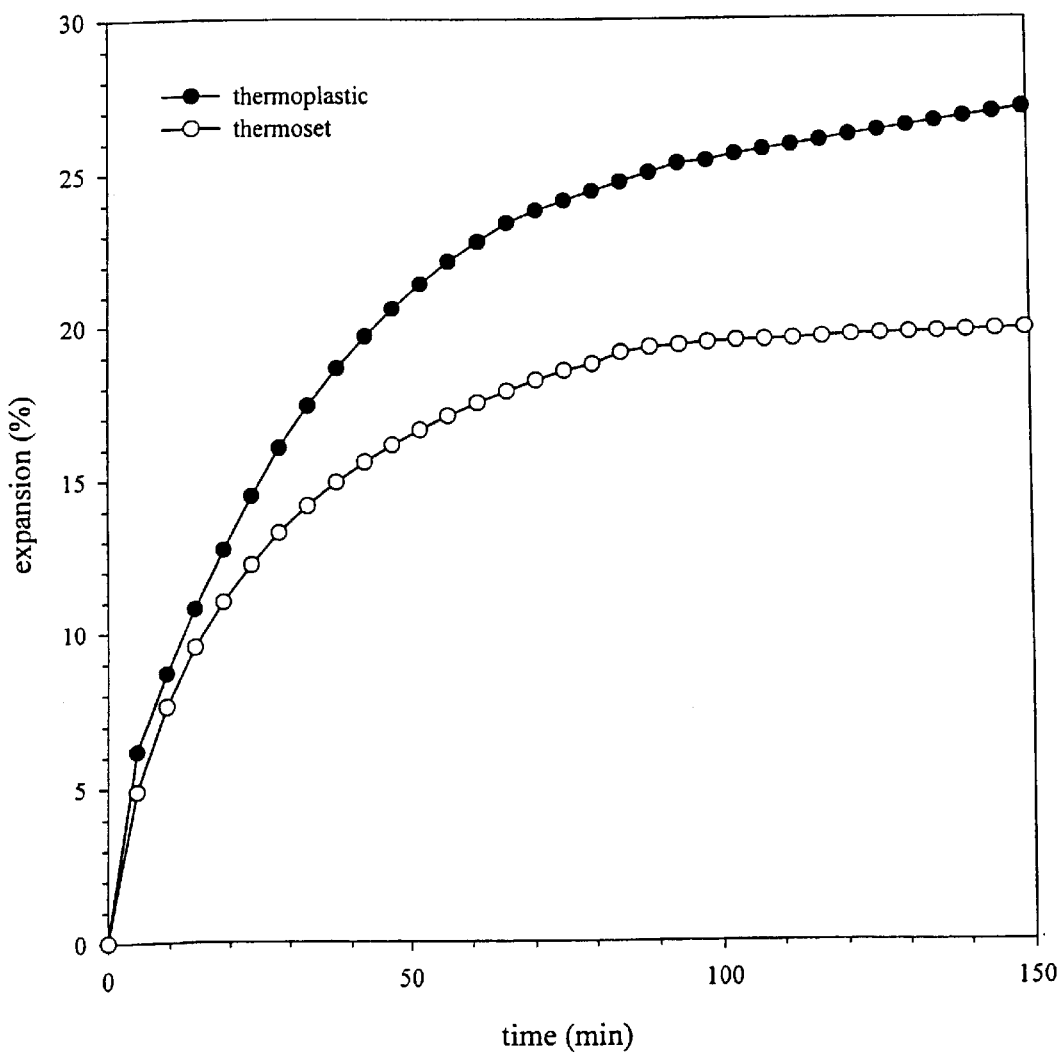
FIG. 7 is a graph depicting the volumetric expansion over time of a thermoset CB/HDPE/EVA conductive polymer composite, constructed according to the present invention, upon immersion in THF relative to a similar thermoplastic version.

The composites, JQ01-P38-TS1 and JQ01-P25-5, were compared for volumetric expansion over immersion time in THF; this data being depicted in FIG. 7. As expected, the crosslinked composite, JQ01-P38-TS1, has lower volumetric expansion when compared to the thermoplastic JQ01-P25-5 composite.

EXAMPLE 4

A reversible electrochemical sensor of the present invention which demonstrates good sensitivity via a reversible change in conductivity in the presence of the vapor of an analyte was made according to the present invention using commercial grades of random copolymer of poly(ethylene-co-vinyl acetate) ("EVA"), HDPE, and furnace grade carbon black using the mixing procedure and electrochemical sensor disc preparation as heretofore described in Example 1. The characteristics of the materials used in this example are set forth in Table 1. The present example, which utilizes the electrochemical sensor of Example 1, demonstrates the reversible change in conductivity of the electrochemical sensor of the present invention when in the presence of THF vapor.

Figure 8:
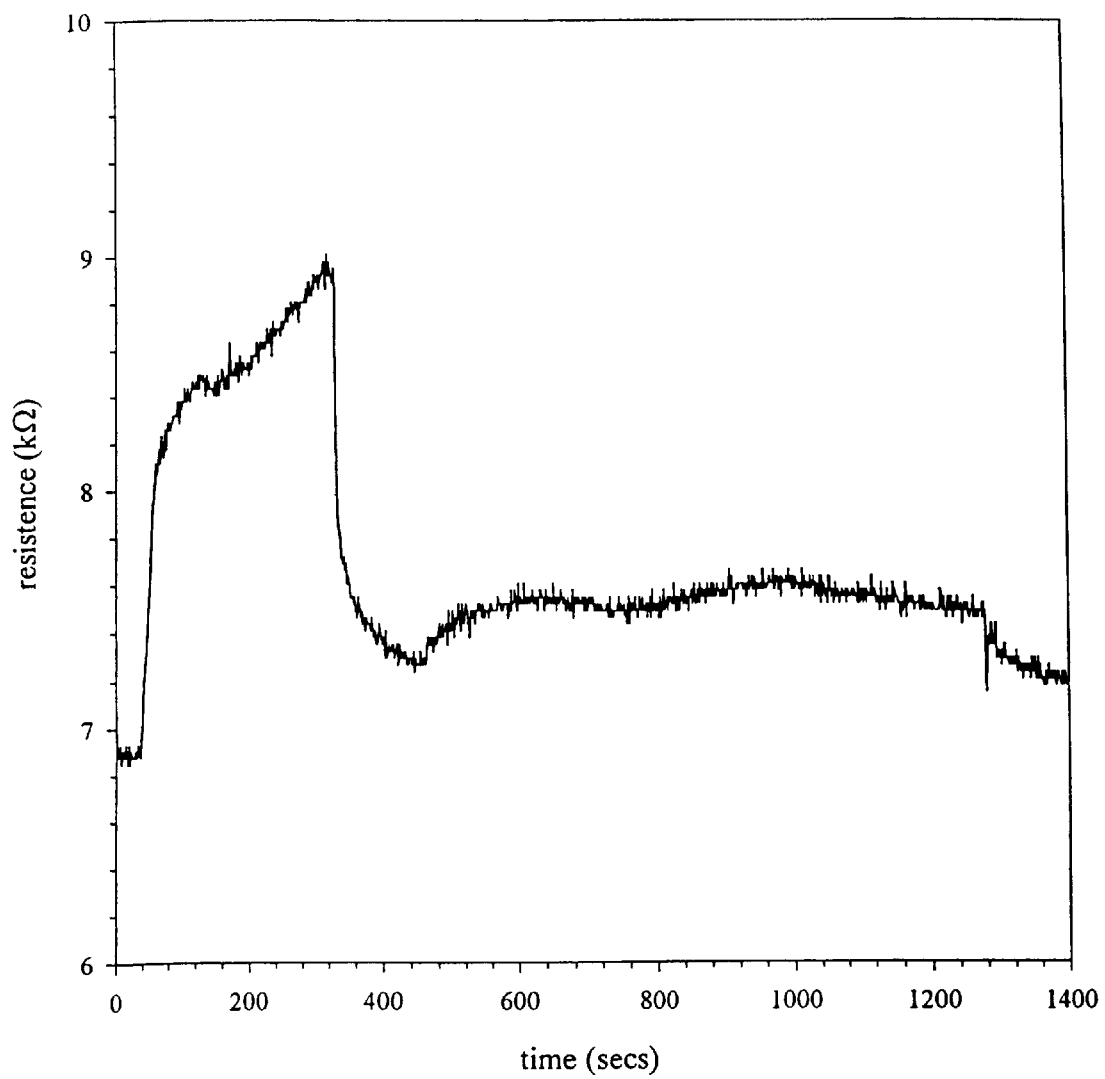
FIG. 8 is a graph depicting the electrochemical response over time of a CB/HDPE/EVA conductive polymer composite, constructed according to the present invention, when exposed to THF vapor.

The electrochemical sensor of the present example was placed in the test circuit of FIG. 2. The electrochemical sensor was placed in a 400 ml beaker filled to the 50 ml mark with THF and exposed to the THF vapors. Referring now to FIG. 8, at 40 seconds, a change in resistance is experienced by the electrochemical sensor when the sensor was lowered into the beaker 12 mm above the surface of the THF due to contact with the THF vapor. The increase in resistance of the electrochemical sensor continued until 360 seconds when the electrochemical sensor was raised to 48 mm above the surface of the THF, where a decrease in the resistance of the electrochemical sensor can be seen. At 460 seconds, the resistance of the electrochemical sensor is seen to increase as the electrochemical sensor is positioned 24 mm above the surface of the THF. Finally, at 1280 seconds, the resistance of the electrochemical sensor decreases, approaching the pre-exposure resistance, as the electrochemical sensor is removed from the presence of THF vapor.

It can be seen from the foregoing examples that a reversible electrochemical sensor having low cost due to the reduction of conductive filler through a multiple percolation approach to compounding, having good sensitivity to the presence and/or immersion in various chemical analytes, and having sensitivity to a chemical analyte tailored by major phase polymer selection has been provided. Further it has been demonstrated that such sensors can be crosslinked, thus providing electrochemical sensors which will maintain their reversibility in the presence or immersion in harsh solvents. Additionally, the electrochemical sensors and method of making same which comprise multiple sensors within one conducting composite material have been provided.

While various embodiments of the invention have been shown and described, it is to be understood that the above-described embodiments are merely illustrative of the invention and other embodiments may be devised by those skilled in the art which will embody the principles of the invention and fall within the spirit and scope thereof.

What is claimed is:

1. A reversible electrochemical sensor for detecting the presence of chemical analytes comprising:
   (a) a conductive polymer composite of an immiscible polymer blend, said blend comprising (1) a conductive filler material, (2) a minor phase material in which said conductive filler material is dispersed in an amount sufficient to generate a continuous conductive network in said minor phase material and forming a binary composite, and (3) a major phase material with an affinity for at least one analyte, said major phase material being a polymer which when mixed with said binary composite will not engage in electrostatic interactions that promote miscibility, said major phase material having said binary composite dispersed therein in an amount sufficient to generate a continuous conductive network in said major phase material and forming a conducive ternary composite having distinct co-continuous phases; and
   (b) a pair of electrodes in electrical contact with said conductive ternary composite, wherein electrical properties of said conductive ternary composite undergo a reversible change when in proximity to at least one analyte.

2. The electrochemical sensor of claim 1, wherein the electrical properties of said conductive ternary composite are selected from the group comprising resistance, conductance, and capacitance.

3. The electrochemical sensor of claim 1, wherein said conductive filler material comprises between about 0.001 percent by weight and about 25 percent by weight of the total conductive polymer composite weight.

4. The electrochemical sensor of claim 1, wherein said amount of conductive filler material dispersed in said minor phase material is not more than 0.5% by weight greater than the amount sufficient to generate a continuous conductive network in said minor phase material; and wherein said amount of binary composite dispersed in said major phase material is not more than 1% by weight greater than the amount sufficient to generate a continuous conductive network in said major phase material.

5. The electrochemical sensor of claim 1, wherein said amount of conductive filler material dispersed in said minor phase material is not more than 1% by weight greater than the amount sufficient to generate a continuous conductive network in said minor phase material; and wherein said amount of binary composite dispersed in said major phase material is not more than 2% by weight greater than the amount sufficient to generate a continuous conductive network in said major phase material.

6. The electrochemical sensor of claim 1, wherein said amount of conductive filler material dispersed in said minor phase material is not more than 2% by weight greater than the amount sufficient to generate a continuous conductive network in said minor phase material; and wherein said amount of binary composite dispersed in said major phase material is not more than 2% by weight greater than the amount sufficient to generate a continuous conductive network in said major phase material.

7. The electrochemical sensor of claim 1, wherein said amount of conductive filler material dispersed in said minor phase material is not more than 5% by weight greater than the amount sufficient to generate a continuous conductive network in said minor phase material; and wherein said amount of binary composite dispersed in said major phase material is not more than 5% by weight greater than the amount sufficient to generate a continuous conductive network in said major phase material.

8. The electrochemical sensor of claim 1, wherein said conductive filler material is selected from the group consisting of carbon black, graphite, metallic particles, carbon fibers, intrinsically conductive polymers, fullerenes, nanotubes, whiskers, and combinations thereof.

9. The electrochemical sensor of claim 1, wherein said minor phase material has a crystallinity of about 20% to about 80%.

10. The electrochemical sensor of claim 1, wherein said minor phase material is a semicrystalline polymer and said major phase material has a crystallinity of about 20% to about 80% such that said conductive polymer composite physically crosslinks through crystalline regions.

11. The electrochemical sensor of claim 1, wherein said conductive polymer composite is exposed to $\beta$ or $\gamma$ radiation for a sufficient time to effect crosslinking of the composite.

12. The electrochemical sensor of claim 1, wherein a hydrolyzable group is grafted onto said major phase material prior to dispersing said minor phase material therein, such that said conductive polymer composite will crosslink on exposure to moisture.

13. The electrochemical sensor of claim 12, wherein said major phase material is a commercially available copolymer which contains a hydrolyzable functionality as part of the copolymer backbone.

14. The electrochemical sensor of claim 1, wherein a hydrolyzable copolymer is created by grafting an unsaturated moiety containing one or more hydrolyzable functionalities to the backbone of said major phase material prior to dispersing said minor phase material in said major phase material.

15. The electrochemical sensor of claim 1, wherein an organic peroxide is added to said major phase material prior to dispersion of said minor phase material, therein, thereby effecting crosslinking with the decomposition of the peroxide and subsequent generation of free radicals at elevated temperatures.

16. The electrochemical sensor of claim 1, wherein said minor phase material is high density polyethylene and said major phase material is comprised of a poly(ethylene-co-vinyl acetate).

17. The electrochemical sensor of claim 16, wherein vinyl acetate content comprises from about 9% to about 45% by weight of said poly(ethylene-co-vinyl acetate), such that an affinity of said poly(ethylene-co-vinyl acetate) for at least one analyte is selectively adjusted by varying said vinyl acetate content of said poly(ethylene-co-vinyl acetate).

18. The electrochemical sensor of claim 1, further comprising means for crosslinking said conductive polymer composite.

19. The electrochemical sensor of claim 1, further comprising:

a second major phase material, said second major phase material having an affinity for a second analyte, wherein said conductive ternary composite is dispersed in an amount sufficient to generate a continuous conductive network in said second major phase material, said second major phase material being selected from that group of polymers which when mixed with said conductive ternary composite will not engage in electrostatic interactions that promote miscibility with said minor phase material or with said major phase material, forming a conductive quaternary composite having distinct co-continuous phases, wherein electrical properties of said conductive quaternary composite undergo a reversible change when in proximity to said second analyte.

20. The electrochemical sensor of claim 19 wherein the electrical properties of said conductive quaternary composite are selected from the group comprising resistance, conductance, and capacitance.

21. The electrochemical sensor of claim 19, further comprising means for crosslinking said conductive quaternary composite.

22. The electrochemical sensor of claim 19, further comprising one or more additional major phase materials, each of said additional major phase materials being polymers having an affinity for additional analytes, said additional major phase materials being polymers which when mixed with each other, with said major phase material, with said second major phase material, and with said minor phase material will not engage in electrostatic interactions that promote miscibility, forming a conducting multi-phase composite having distinct co-continuous phases, wherein the conductivity of said conducting multi-phase composite undergoes a reversible change when in proximity to one of said additional analytes.

23. The electrochemical sensor of claim 22, further comprising means for crosslinking said conducting multi-phase composite.

24. The electrochemical sensor of claim 1, wherein said conductive polymer composite further comprises a material selected from the group consisting of antioxidants, nucleating agents, coupling agents, ultraviolet absorbers, ultraviolet stabilizers, pigments, dyes, reinforcing fillers, slip agents, plasticizers, processing aids, lubricants, viscosity control agents, tackifiers, anti-blocking agents, surfactants, extender oils, metal deactivators, voltage stabilizers, flame retardant fillers, cross-linking agents, boosters, catalysts, smoke suppressants, and combinations thereof in the amount of about 0.05% by weight to about 50% by weight of said conductive polymer composite.

25. A method of producing a reversible electrochemical sensor for detecting the presence of chemical analytes comprising:
    mixing a minor phase polymer having a melting temperature at a temperature greater than or equal to said melting temperature of said minor phase polymer;
    mixing a conductive filler with said minor phase polymer in an amount greater than or equal to an amount required to generate a continuous conductive network in said minor phase polymer for a time and at a sufficient speed to insure a uniform distribution of said conductive filler in said minor phase polymer, thereby forming a binary composite having a melting temperature;
    mixing a major phase material having a melting temperature with said binary composite in a mixer preheated to at least the melting temperature of said major phase material and the melting temperature of said binary composite, for a time and at a sufficient speed to insure a uniform distribution of said binary composite in said major phase material, such that a weight ratio of said binary composite to said major phase material is sufficient for said binary composite to be equal to or greater than an amount required to generate a continuous conductive network in said major phase material, said major phase material being selected from that group of polymers which when mixed with said binary composite will not engage in electrostatic interactions which promote miscibility, such that a conductive ternary composite with co-continuous phases is formed; and
    securing a pair of electrodes to said conductive ternary composite, said pair of electrodes being in electrical contact with said conductive ternary composite.

26. The method of claim 25, further comprising annealing said binary composite, thereby increasing the crystalline phase and resulting in a lower percolation threshold for the binary composite, thereby reducing the total amount of required conductive filler in the total composite.

27. The method of claim 25, further comprising optimizing the surface area to volume ratio of said binary composite prior to mixing with said major phase material, thereby lowering the percolation threshold necessary to generate a continuous conductive network.

28. The method of claim 25, further comprising: crosslinking said conductive ternary composite.

29. The method of claim 25 further comprising: annealing said conductive ternary composite prior to securing said pair of electrodes, thereby increasing the conductivity of said conductive ternary composite.

30. The method of claim 25 further comprising: mixing a second major phase material having a melting temperature with said conductive ternary composite in said mixer preheated to above the melting temperature of said second major phase material and said conductive ternary composite, for a time and at a sufficient speed to insure a uniform distribution of said conductive ternary composite in said second major phase material, such that a weight ratio of said conductive ternary composite to said second major phase material is sufficient for said conductive ternary composite to be equal to or greater than an amount required to generate a continuous conductive network in said second major phase material, said second major phase material being selected from that group of polymers which when mixed with said conductive ternary composite will not engage in electrostatic interactions which promote miscibility with said binary composite or with said major phase material, such that a conductive quaternary composite with distinct co-continuous phases is formed, prior to securing said pair of electrodes.

31. The method of claim 30, further comprising: annealing said conductive quaternary composite, said conductive ternary composite, and/or said binary composite thereby increasing the conductivity of said composite.

32. The method of claim 30, further comprising: crosslinking said conductive quaternar composite.

33. The method of claim 30, further comprising the additional steps of mixing additional major phase materials with said conductive quaternary composite in a mixer preheated to above the melting temperature of each additional major phase material, said additional major phase materials being polymers which when mixed with each other, said second major phase material, said major phase material, said minor phase polymer and said conductive filler will not engage in electrostatic interactions that promote miscibility, said additional major phase materials each having an affinity for additional analytes, such that a multi-phase immiscible conducting polymer composite having distinct co-continuous phases is formed which undergoes a reversible change when in proximity to each of said additional analytes.

34. The method of claim 33 further comprising crosslinking said multi-phase immiscible conducting polymer composite.

35. The method of claim 25, further comprising: adding material selected from the group consisting of antioxidants, nucleating agents, coupling agents, ultraviolet absorbers, ultraviolet stabilizers, pigments, dyes, reinforcing fillers, slip agents, plasticizers, processing aids, lubricants, viscosity control agents, tackifiers, anti-blocking agents, surfactants, extender oils, metal deactivators, voltage stabilizers, flame retardant fillers, boosters, catalysts, smoke suppressants, and combinations thereof to said conductive ternary composite in the amount of about 0.05% by weight to about 50% by weight of said conductive ternary composite.

* * * * *

UNITED STATES PATENT AND TRADEMARK OFFICE
CERTIFICATE OF CORRECTION

PATENT NO.    : 6,315,956 B1
DATED         : November 13, 2001
INVENTOR(S)   : Foulger It is certified that error appears in the above-identified patent and that said Letters Patent is hereby corrected as shown below:

Column 4,
Line 24, change "p," to -- $p_c$ --;

Column 5,
Line 52, change "$p_c = p_{60} p_{62}$" to -- $p_c = p_\alpha p_\beta$ --

Column 18,
Line 6, change "Elvax 263" to -- Elvax 265 --;

Column 26,
Line 59, change "quarternar" to -- quarternary --.

Signed and Sealed this

Second Day of April, 2002

*Attest:*

JAMES E. ROGAN
*Attesting Officer*            *Director of the United States Patent and Trademark Office*